United States Patent [19]
Castellano et al.

[11] Patent Number: 5,593,390
[45] Date of Patent: Jan. 14, 1997

[54] MEDICATION DELIVERY DEVICE WITH A MICROPROCESSOR AND CHARACTERISTIC MONITOR

[75] Inventors: Thomas P. Castellano; Robert Schumacher, both of Beverly Hills, Calif.

[73] Assignee: Visionary Medical Products, Inc.

[21] Appl. No.: 396,420

[22] Filed: Feb. 28, 1995

Related U.S. Application Data

[63] Continuation-in-part of Ser. No. 350,405, Dec. 5, 1994, which is a continuation-in-part of Ser. No. 208,636, Mar. 9, 1994, Pat. No. 5,536,249.

[51] Int. Cl.⁶ .............................. A61M 5/00; A61M 5/20
[52] U.S. Cl. ......................... 604/187; 604/156; 604/207; 604/232; 128/DIG. 1
[58] Field of Search .................................. 604/189, 156, 604/187, 131, 154, 232, 66, 207, 208, 218; 128/632, 639, 771, DIG. 1, 670

[56] References Cited

U.S. PATENT DOCUMENTS

| | | |
|---|---|---|
| 1,997,129 | 4/1935 | Taylor et al. . |
| 2,221,739 | 11/1940 | Reiter . |
| 2,605,763 | 8/1952 | Smoot . |
| 2,632,445 | 3/1953 | Kas . |
| 2,695,023 | 11/1954 | Brown . |
| 2,718,299 | 9/1955 | Atwater et al. . |
| 3,110,310 | 11/1963 | Cislak . |
| 3,141,583 | 7/1964 | Mapel et al. . |
| 3,293,749 | 12/1966 | George et al. . |
| 3,348,545 | 10/1967 | Sarnoff et al. . |
| 3,481,510 | 12/1969 | Allen, Jr. . |
| 3,517,668 | 6/1970 | Brickson . |

(List continued on next page.)

FOREIGN PATENT DOCUMENTS

| | | |
|---|---|---|
| 55604/86 | 10/1987 | Australia . |
| 1103314 | 6/1981 | Canada . |
| 0037696 | 10/1981 | European Pat. Off. . |
| 0058536 | 8/1982 | European Pat. Off. . |
| 0143895 | 6/1985 | European Pat. Off. . |
| 0416975 | 3/1991 | European Pat. Off. . |
| 1149735 | 12/1957 | France . |
| 1170312 | 1/1959 | France . |
| 1445659 | 6/1966 | France . |
| 2418642 | 9/1979 | France . |
| 2557445 | 5/1985 | France . |
| 730971 | 12/1942 | Germany . |
| 1070784 | 12/1959 | Germany . |
| 22140 | 10/1961 | Germany . |
| 293302 | 9/1953 | Switzerland . |
| 1225495 | 3/1971 | United Kingdom . |
| 1574267 | 9/1980 | United Kingdom . |
| 2109690 | 2/1982 | United Kingdom . |
| 8502546 | 6/1985 | WIPO . |
| 8601728 | 3/1986 | WIPO . |
| 9213583 | 8/1992 | WIPO . |

OTHER PUBLICATIONS

PCT Written Opinion issued by the European Patent Office on Nov. 3, 1995.
Search Report for PCT/US95/01727, mailed Jun. 20, 1995.
*Annual International Conference of the IEEE Engineering in Medicine and Biology Society,* "An Optical and RF Telemetry Drug Injection Control and ECG System for Awake Small Animal Studies", vol. 13, No. 5, 1991.

*Primary Examiner*—Randall L. Green
*Assistant Examiner*—A. T. Nguyen
*Attorney, Agent, or Firm*—Loeb & Loeb LLP

[57] ABSTRACT

A medication delivery device, such as a pen-type injector, jet injector, medication pump, inhaler, spray or the like has a microprocessor coupled to the device that records the date, the time, and the amount of each medication administration. The microprocessor may also be coupled to a display to indicate the amount of medication to be administered. The medication delivery device can also be coupled with a blood characteristic monitor to analyze characteristics of the blood. This provides a single, all-in-one device that performs a variety of functions, and requires only a minimum of space. The medication delivery device may also use a disposable needle that substantially eliminates or reduces bleeding from an opening in the skin at the injection site.

44 Claims, 26 Drawing Sheets

U.S. PATENT DOCUMENTS

| | | |
|---|---|---|
| 3,583,399 | 6/1971 | Ritsky . |
| 3,894,663 | 7/1975 | Carhart et al. . |
| 3,977,574 | 8/1976 | Thomas . |
| 4,022,207 | 5/1977 | Citrin . |
| 4,099,548 | 7/1978 | Sturm et al. . |
| 4,114,619 | 9/1978 | Wagner . |
| 4,139,008 | 2/1979 | Wagner . |
| 4,146,029 | 3/1979 | Ellinwood, Jr. . |
| 4,169,474 | 10/1979 | Wagner . |
| 4,284,077 | 8/1981 | Wagner . |
| 4,333,458 | 6/1982 | Margulies et al. . |
| 4,393,870 | 7/1983 | Wagner . |
| 4,395,921 | 8/1983 | Oppenlander . |
| 4,413,760 | 11/1983 | Paton . |
| 4,415,101 | 11/1983 | Shapiro et al. . |
| 4,425,121 | 1/1984 | Young et al. . |
| 4,435,173 | 3/1984 | Siposs et al. . |
| 4,444,560 | 4/1984 | Jacklich . |
| 4,457,712 | 7/1984 | Dragan . |
| 4,470,317 | 9/1984 | Sabloewski et al. . |
| 4,475,905 | 10/1984 | Himmelstrup . |
| 4,498,904 | 2/1985 | Turner et al. . |
| 4,526,294 | 7/1985 | Hirschmann et al. . |
| 4,529,401 | 7/1985 | Leslie et al. ............................ 604/131 |
| 4,538,616 | 9/1985 | Rogoff .................................... 604/66 X |
| 4,573,970 | 3/1986 | Wagner . |
| 4,581,022 | 4/1986 | Leonard et al. . |
| 4,592,745 | 6/1986 | Rex et al. ............................. 604/211 |
| 4,600,403 | 7/1986 | Wagner . |
| 4,613,328 | 9/1986 | Boyd ...................................... 604/156 |
| 4,659,327 | 4/1987 | Bennett et al. . |
| 4,664,128 | 5/1987 | Lee . |
| 4,710,172 | 12/1987 | Jacklich et al. . |
| 4,710,178 | 12/1987 | Leonard et al. . |
| 4,820,287 | 4/1989 | Leonard . |
| 4,865,591 | 9/1989 | Sams . |
| 4,883,472 | 11/1989 | Michel .................................... 604/208 |
| 4,936,833 | 6/1990 | Sams ...................................... 604/232 |
| 4,950,246 | 8/1990 | Muller .................................... 604/154 |
| 4,959,056 | 9/1990 | Dombrowski et al. ................. 604/186 |
| 4,998,570 | 3/1991 | Strong . |
| 5,024,656 | 6/1991 | Gasaway et al. ......................... 604/70 |
| 5,047,044 | 9/1991 | Smith et al. . |
| 5,050,612 | 9/1991 | Matsumura ............................ 128/670 |
| 5,069,668 | 12/1991 | Boydman ............................... 604/121 |
| 5,085,642 | 2/1992 | Sarnoff et al. .......................... 604/134 |
| 5,092,842 | 3/1992 | Bechtold et al. ....................... 604/135 |
| 5,102,393 | 4/1992 | Sarnoff et al. .......................... 604/136 |
| 5,104,380 | 4/1992 | Holman et al. ......................... 604/117 |
| 5,112,317 | 5/1992 | Michel ................................ 604/232 X |
| 5,114,406 | 5/1992 | Gabriel et al. .......................... 604/136 |
| 5,139,484 | 8/1992 | Hazon et al. . |
| 5,180,371 | 1/1993 | Spinello . |
| 5,226,895 | 7/1993 | Harris ..................................... 604/208 |
| 5,226,896 | 7/1993 | Harris ..................................... 604/211 |
| 5,244,461 | 9/1993 | Derlien . |
| 5,244,465 | 9/1993 | Michel .................................... 604/208 |
| 5,249,548 | 10/1993 | Karkar et al. ....................... 128/771 X |
| 5,256,157 | 10/1993 | Samiotes et al. . |
| 5,279,294 | 1/1994 | Anderson et al. .................. 128/632 X |
| 5,279,585 | 1/1994 | Balkwill ................................. 604/207 |
| 5,279,586 | 1/1994 | Balkwill ................................. 604/207 |
| 5,383,865 | 1/1995 | Michel . |
| 5,425,716 | 6/1995 | Kawasaki et al. . |
| 5,429,602 | 7/1995 | Hauser . |

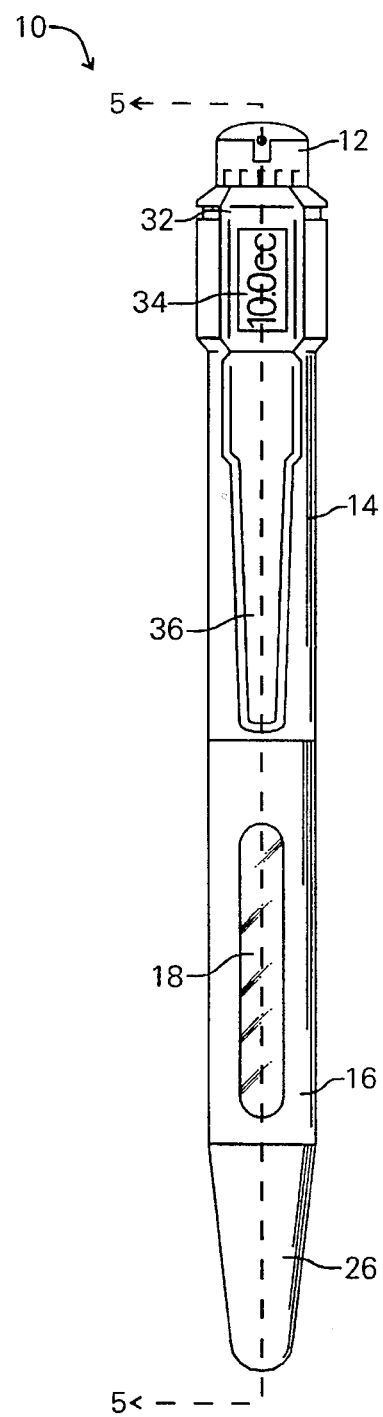
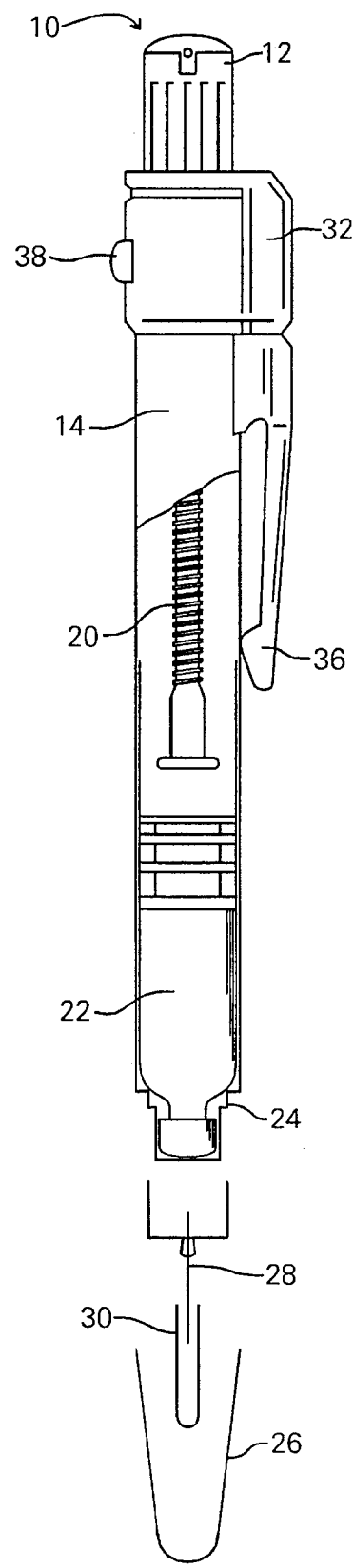
FIG. 2
FIG. 3

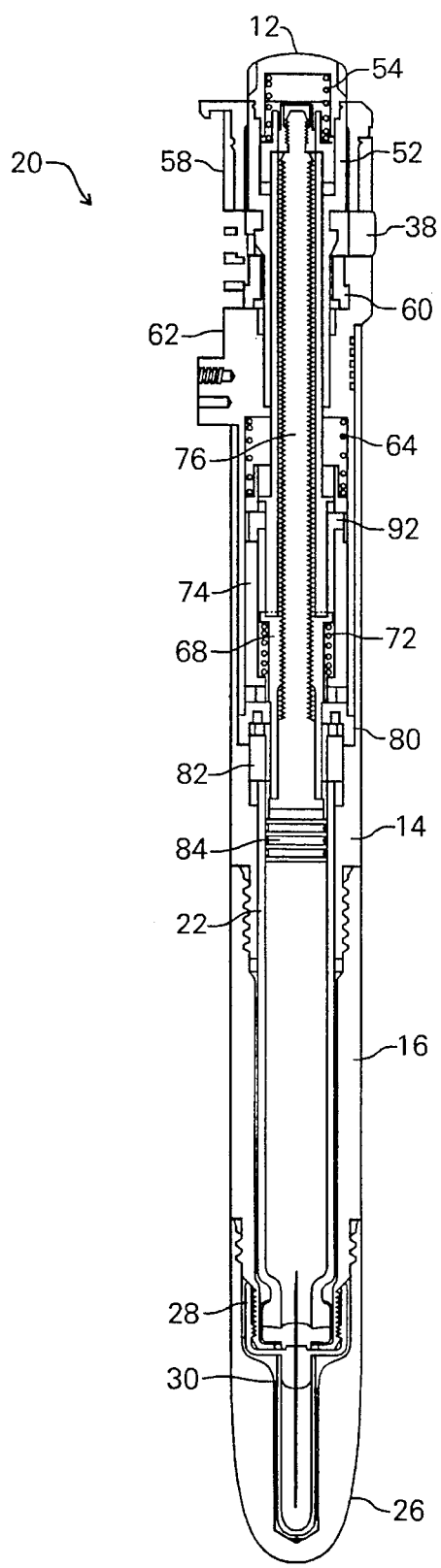
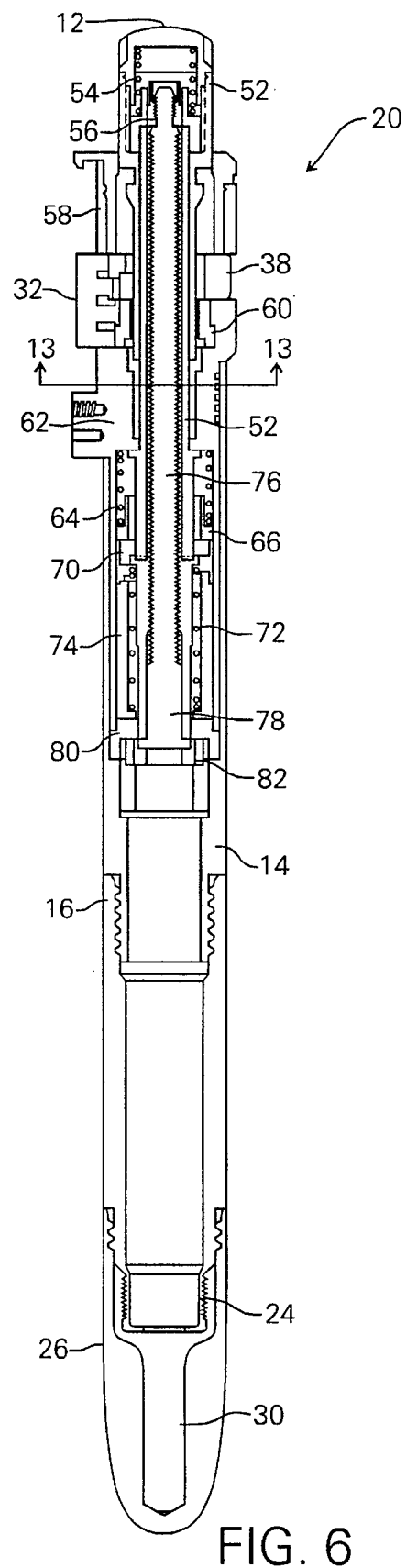
FIG. 5
FIG. 6

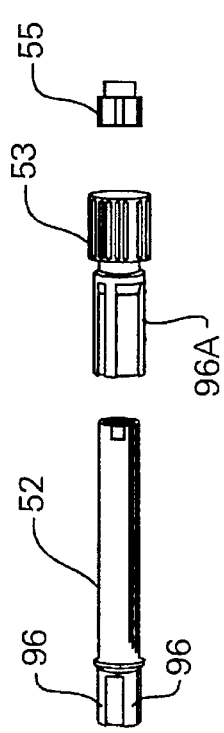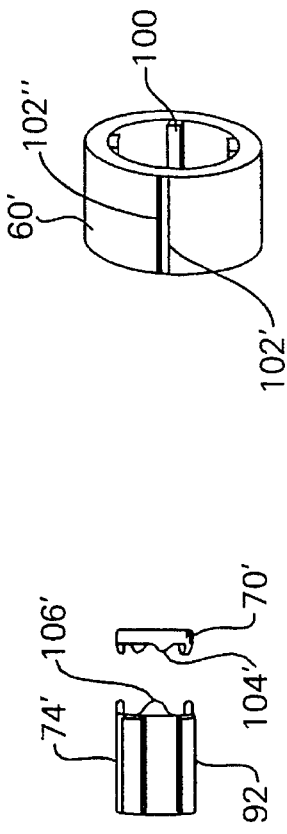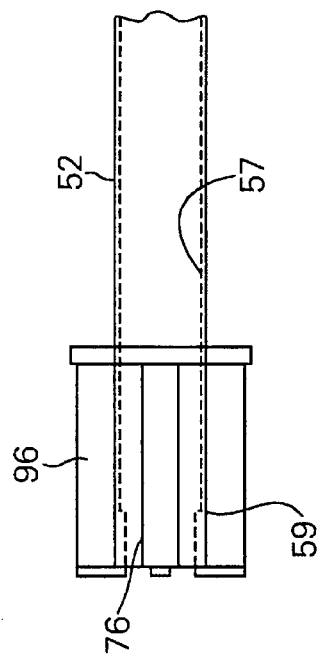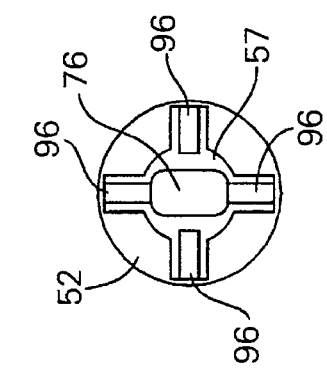
FIG. 7(d)
FIG. 7(f)
FIG. 7(c)
FIG. 7(b)
FIG. 7(e)

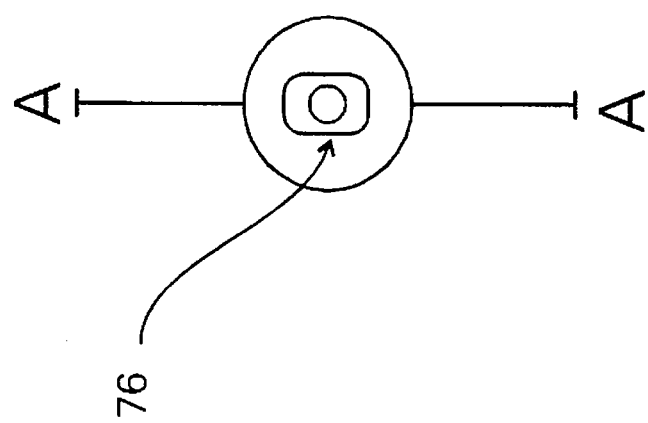
Fig. 7(h)
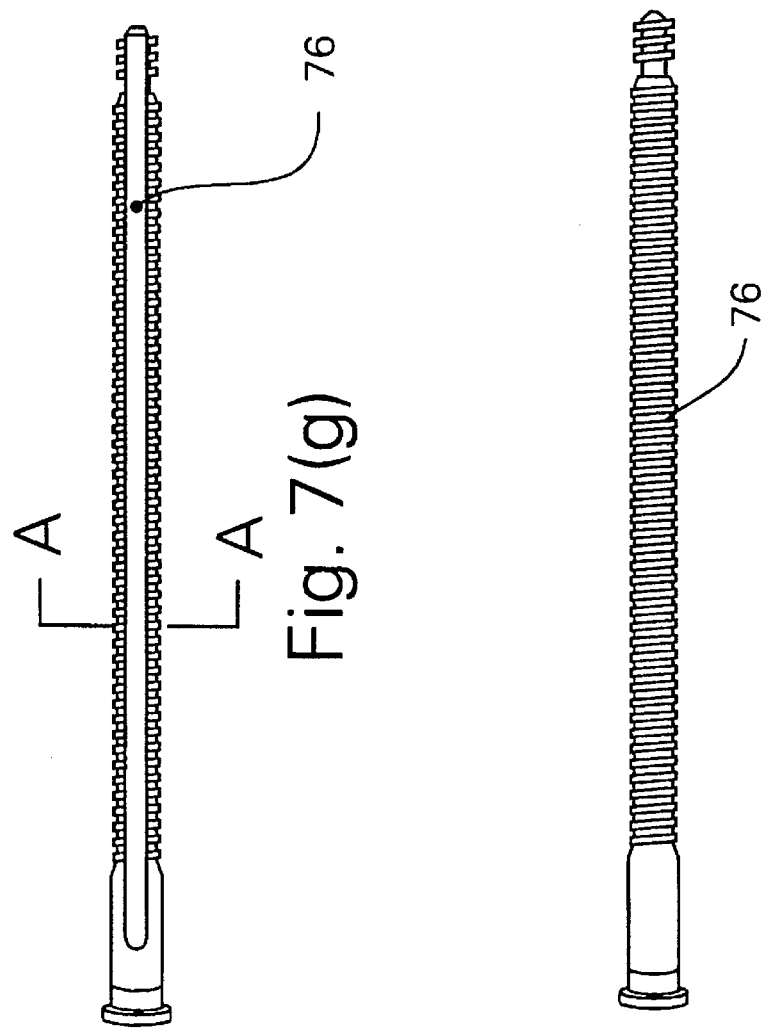
Fig. 7(g)
Fig. 7(i)

BLOOD GLUCOSE (mg/dL) INSULIN LOG

| Name: Good, Johnny B. | Report Date: 12-31-93 |
|---|---|
| I.D. or Chart # | Report Time: 13:50 |
| Phys/Inst: Cedars S. | Report Span: 12-24 to 12-30-93 |

|  | Breakfast | | Lunch | | Dinner | | Snack |
|---|---|---|---|---|---|---|---|
|  | Pre | Post | Pre | Post | Pre | Post | |
| No. of Readings | 7 | 0 | 7 | 0 | 7 | 0 | 7 |
| Std. Deviation | 51.0 | | 42.0 | | 61.0 | | 29.0 |
| Average | 99.3 | | 113.4 | | 130.4 | | 86.0 |

FIG. 24(a)

Blood Glucose Chart:

| | BLOOD GLUCOSE | | | | | | | |
|---|---|---|---|---|---|---|---|---|
| | Breakfast | | Lunch | | Dinner | | Snack | Other |
| | Pre | Post | Pre | | Pre | Post | | |
| 12-24-93 Fri | 06:30 190 | | 11:24 101 | | 16:41 122 | | 21:25 77 | |
| 12-25-93 Sat | 06:41 47 | | 11:20 146 | | 16:20 137 | | 21:15 123 | |
| 12-26-93 Sun | 06:30 59 | | 11:25 113 | | 16:36 156 | | 21:30 111 | |

FIG. 24 (b)

Insulin Chart:

| | INSULIN | | | |
|---|---|---|---|---|
| | Breakfast | Lunch | Dinner | Evening |
| 12-24-93 Fri | 06:39 R-3 L-7 | 11:38 R-6 L-6 | 16:56 R-13 L-11 | 21:37 R-7 L-12 |
| 12-25-93 Sat | 06:42 R-2 L-5 | 11:24 R-3 L-6 | 16:30 R-10 L-10 | 21:33 R-6 L-10 |
| 12-26-93 Sun | 06:36 R-4 L-6 | 11:30 R-6 L-6 | 16:40 R-8 L-12 | 21:40 R-8 L-10 |

FIG. 24 (c)

Markers Chart:

| | MARKERS | | | |
|---|---|---|---|---|
| | Symptom | Meal | Exercise | Special |
| 12-24-93 Fri | | 17:15 inc | | |
| 12-25-93 Sat | 06:00 | | 18:30 | |
| 12-26-93 Sun | | | 18:15 inc | |

FIG. 24 (d)

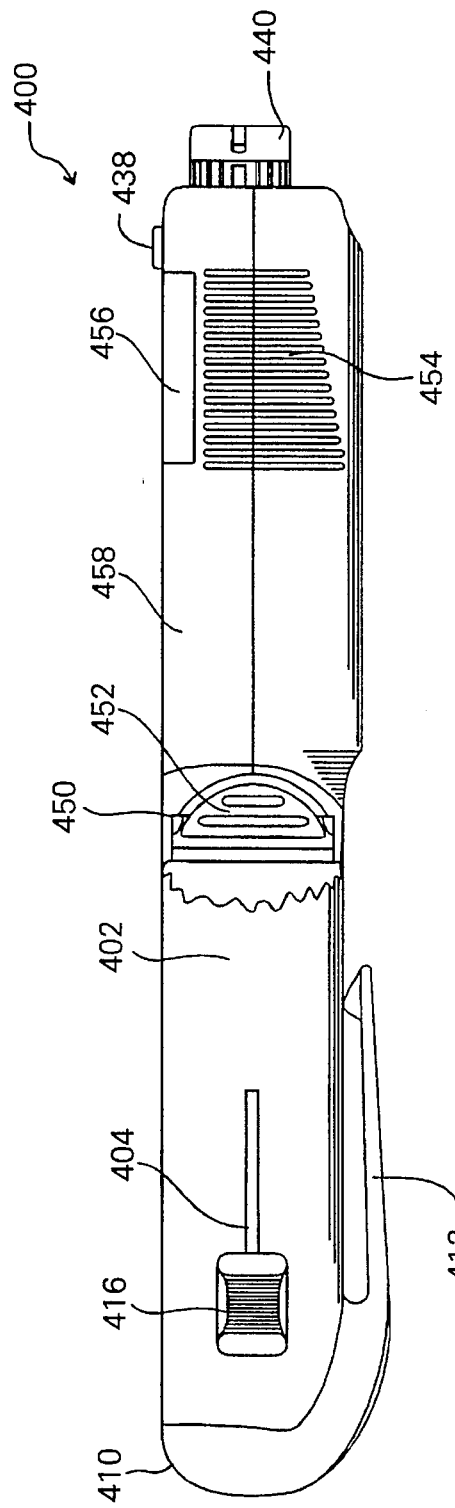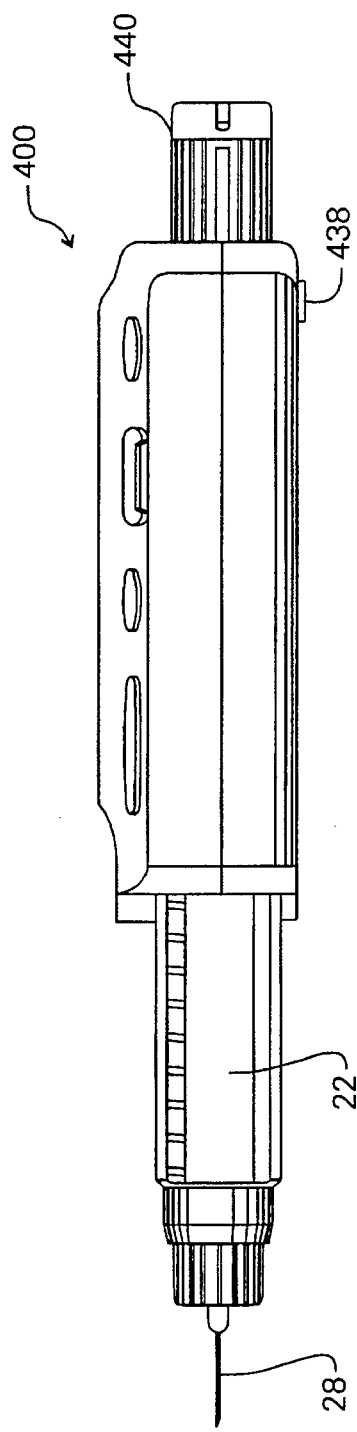
FIG. 25(b)
FIG. 25(c)

MEDICATION DELIVERY DEVICE WITH A MICROPROCESSOR AND CHARACTERISTIC MONITOR

RELATED APPLICATIONS

This is a continuation-in-part of U.S. patent application Ser. No. 08/350,405, filed Dec. 5, 1994 now pending, which is a continuation-in-part of U.S. patent application Ser. No. 08/208,636, filed Mar. 9, 1994 now U.S. Pat. No. 5,536,249.

FIELD OF THE INVENTION

This invention relates to pen-type injectors for injecting medications or other injectable substances and, in particular embodiments, a pen-type injector for injecting insulin. In preferred embodiments, the pen-type injector utilizes a microprocessor to record injection information and a monitor to measure blood characteristics. Further embodiments of the invention also relate to other types of medication delivery devices that can utilize a microprocessor and a characteristic monitor.

BACKGROUND OF THE INVENTION

Home treatment methods for the control and management of various diseases are becoming more popular. For instance, high success rates for treatment of diabetes have been achieved when a diabetic patient controls the disease by self-testing blood glucose levels and administering a correct dose of insulin. The doctor works with the patient to determine the best regimen of diet, exercise, and insulin dose to maintain a target blood glucose level.

Between doctor's office visits, the patient is responsible for carrying out the prescribed regimen, which includes frequent blood testing and insulin administration using a syringe, needleless injector, pen-type injector or insulin pump. The patient and doctor select a blood glucose monitor based on desired monitor features, suitability for the patient, perceived accuracy, and ease of use.

Home diabetes therapy requires personal discipline of the user, is time consuming, requires an appropriate location, and the proper instruments and accessories. Therefore, it is highly desirable that the home therapy regimen cause minimal inconvenience and changes in the patient's lifestyle. Many past therapy regimens and devices have failed to provide the convenience and minimum changes to the patient's lifestyle, and thus the compliance with the medical regimens have been less than satisfactory.

Traditionally, for out-patient and in-home patient care, medication has been injected by a syringe, wherein the user has to insert the needle of the syringe into a separate medication vial to withdraw medication. Once the medication is withdrawn from the vial, the user removes any air bubbles and extra medication, and then injects the medication.

Typical syringes suffer from many drawbacks. For instance, they may not be preloaded with medication; thus, requiring the user to carry a separate medication vial. Moreover, people with dexterity disorders often have difficulty lining up the needle portion of the syringe with the rubber septum on the medication vial. This can lead to unintentional needle pricks or excessive time being required to complete an injection, both of which tend to inhibit compliance with a medical regimen. Also, it is often difficult for children or people with failing eyesight to line up the medication with the proper dosage line on the outer casing of the syringe. Furthermore, the user of the syringe is typically responsible for manually recording the date, the time and the dosage in a separate log book so that the doctor can monitor the user's compliance with the prescribed medical regimen.

Another drawback to the traditional syringe is that a syringe is difficult to use in public places. For instance, many schools do not allow students to carry syringes. This prohibition against syringes can cause excessive delays between injections, and thus could complicate a user's medical condition. Moreover, there is also a social stigma attached to using a syringe, since it raises connotations of drug abuse. These drawbacks have been one of the principal reasons why users have abandoned medical regimens requiring the use of syringes in social settings.

As an alternative, pen-type injectors have been developed. The pen-type injectors often use prepackaged insulin. However, these devices have been inherently inaccurate and undependable due to their difficult to read scales and inadequately designed mechanical injection systems. For example, typical pen-injectors require multiple and repeated activations of the injector mechanism to administer a desired dosage. Thus, during administration of an injection, the user must keep track of the number of activations (i.e., depressions) to determine when the required dosage has been delivered.

Another disadvantage to pen-type injectors is that typical disposable needles used on pen-type injectors cause bleeding during the administration of an injection. This results from the disposable needle spreading the opening in the skin at the injection site, thereby allowing the skin to bleed. This bleeding from traditional disposable needles can discourage users from following the medical regimen, and the bleeding also increases the likelihood of spreading infectious diseases.

Often a user who takes certain medications, such as insulin, in a home therapy regimen must also monitor the level of glucose present in the blood at periodic intervals. The test results are used to determine when another injection should be administered or to determine how the user is responding to prior injections. Typically, the blood monitor is a separate device that the user must carry along with the insulin injector or syringe. To use the blood monitor the user must lance a portion of the body (i.e., typically a finger) and take a sample that is analyzed by the monitor. The user then manually records the results, the time and the date in a separate log book.

SUMMARY OF THE DISCLOSURE

According to embodiments of the present invention, a medication delivery device, such as a pen-type injector, medication pump, inhaler, spray or the like, has a processor coupled to the medication delivery device that records the date, the time, and the amount of each medication delivery. The processor may also be coupled to a display to indicate the amount of medication to be delivered.

In particular embodiments, a medication delivery device includes a delivery mechanism that has an actuator for setting the dosage and administering a dosage of a medication contained within the medication delivery device. The medication delivery device also has a processor coupled to the actuator of the delivery mechanism to determine a value equal to the dosage set by the actuator of the delivery mechanism, and a memory device coupled to the processor to store the value determined by the processor. In further embodiments, the medication delivery device also has a receptacle capable of holding the medication and the delivery mechanism further includes a drive mechanism coupled between the actuator and the receptacle to deliver the set dosage of the medication. In other embodiments, the medication delivery device also includes a display device to display the value equal to the dosage determined by the processor and a clock circuit for determining the time. In preferred embodiments, the medication delivery device includes a data port for transferring information to and from the processor and memory device to an external device.

In particular embodiments of the present invention, a medical device includes a medication delivery device that is also coupled with a characteristic monitor to analyze characteristics of a sample. This provides a single, all-in-one device that performs a variety of functions, and requires only minimal space.

In particular embodiments, a medical device includes a medication delivery device for delivering a dosage of a medication, a blood characteristic monitor for analyzing a blood sample, and a processor coupled to the medication delivery device and the blood characteristic monitor. The processor determines a value equal to the dosage of the medication to be delivered by the medication delivery device. The processor also determines blood characteristics from a blood sample analyzed by the blood characteristic monitor.

In further embodiments, the medical device also includes a memory device coupled to the processor to store the value equal to the dosage and the blood characteristics determined by the processor. In preferred embodiments, the medical device includes a data port for transferring information to and from the processor and memory device to an external device and a clock circuit for tracking the time.

According to another embodiment of the invention, a pen-type injector utilizes a disposable needle that substantially eliminates or reduces bleeding from an opening in the skin at the injection site. Also in other embodiments, the pen-type injector uses a direct drive mechanism for injecting the medication with a single depression of an actuator knob. Moreover, the actuator knob is rotatable to adjust the amount of medication that is injected.

In particular embodiments, a disposable needle for a pen-type injector has a base adapted to be coupled to a pen-type injector, an injection needle having an injection end and a connecting end, and a hollow cylindrical cover having an open end and an opposite connecting end. Both the connecting end of the injection needle and the opposite connecting end of the hollow cylindrical cover are coupled to the base such that the injection needle is disposed in the center of the open end of the hollow cylindrical cover with the connecting end of the injection needle inside the hollow cylindrical cover below the open end of the hollow cylindrical cover. Moreover, the injection end of the injection needle extends beyond the open end of the hollow cylindrical cover.

According to a further embodiment of the present invention, a watch monitor includes a blood characteristic monitor and a clock that performs as a wrist watch. The watch monitor utilizes a high quality blood analysis device that can record detailed information on blood analysis results and injections. Moreover, the device can be worn easy and unobtrusively on a wrist so that typical time and alarm functions are combined with the blood characteristic monitor to coordinate the blood testing regimen and reduce the number of items a user must carry. Thus, a user has improved detailed record keeping, regimen alarms and reminders, blood characteristic analysis capabilities, and time keeping functions in a single, all-in-one device.

In particular embodiments of the present invention, a portable blood monitor includes a housing of suitable size and configuration to be worn on a wrist, a clock contained in the housing for measuring time, and a blood characteristic monitor contained in the housing for analyzing a blood sample. The portable blood monitor also includes a processor coupled to the blood characteristic monitor and the clock. The processor determines blood characteristics based on the analyzed blood sample from the blood characteristic monitor, and the processor uses the measure of the time from the clock to identify when the blood characteristics were determined. In further embodiments, the portable blood monitor also includes a memory storage device coupled to the processor for storing the measure of time from the clock and the blood characteristics determined by the processor, and a display device to display the measure of the time from the clock and the blood level characteristics determined by the processor. In preferred embodiments, the portable blood monitor includes a data port for transferring information to and from the processor and memory device to an external device and the data port may utilize infrared communication technology to transfer the information.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 2 is a front perspective view of the embodiment of the pen-type injector shown in FIG. 1.

FIG. 3 is a partial cross-sectional and exploded side view of the pen-type injector shown in FIG. 2.

FIG. 5 is a cross-sectional view of the pen-type injector embodiment as shown along the line 5—5 in FIG. 2.

FIG. 6 is another cross-sectional view of the pen-type injector shown in FIG. 5, with the actuator in the released position.

FIGS. 7(a)–7(i) show exploded views and details of a drive mechanism in accordance with an embodiment of the present invention. FIG. 7(a) is an exploded view of the drive mechanism. FIGS. 7(b) and 7(b) are an alternative embodiment for a portions of the drive mechanism. FIG. 7(d) is a further exploded view of an actuator knob drive shaft shown in FIG. 7(a). FIGS. 7(e)–7(f) show various views of a keyway bore in the actuator knob drive shaft shown in FIG. 7(a). FIGS. 7(g)–7(i) show various views of the threaded drive shaft shown in FIG. 7(a).

FIGS. 24(a)–24(d) are diagrams of typical reports obtained from the embodiment shown in FIGS. 22 and 23 or other embodiments.

FIGS. 25(a)–25(e) are views of a pen-type injector with a blood characteristic monitor in accordance with an embodiment of the present invention.

DETAILED DESCRIPTION OF THE PREFERRED EMBODIMENTS

Figure 1:
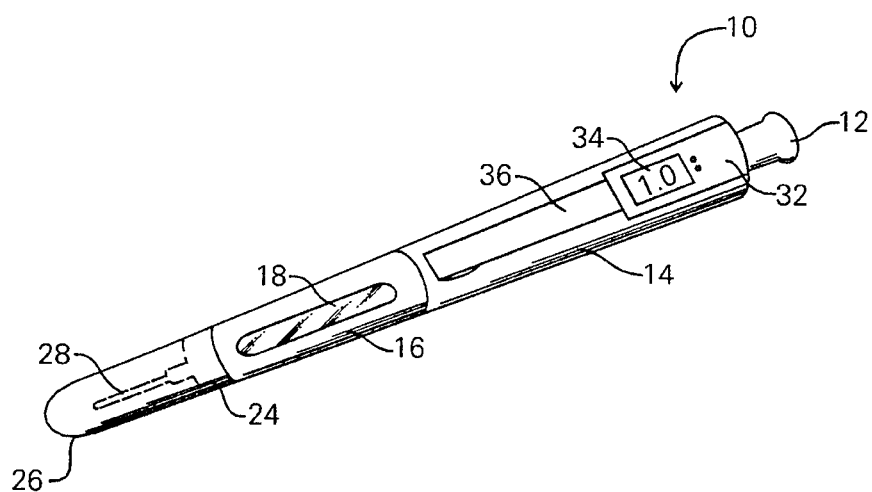
FIG. 1 is a perspective view of a pen-type injector in accordance with an embodiment of the present invention.

As shown in the drawings for purposes of illustration, the invention is embodied in a medication delivery device utilizing a microprocessor. In particular embodiments of the present invention, the medication delivery device further includes a characteristic monitor to measure characteristics of a sample from a patient. In further embodiments, the medication delivery device uses a direct drive injection mechanism, and may include a disposable needle which substantially eliminates or reduces bleeding caused from administration of an injection. In other embodiments, a blood characteristic monitor is contained within a wrist watch sized device that combines blood characteristic monitoring, time keeping and information recording in a single, all-in-one device that is worn on a user's wrist.

In preferred embodiments of the present invention, the medication delivery device is used to deliver insulin, and the characteristic monitor is used to determine the amount of glucose present in a blood sample. However, it will be recognized that further embodiments of the invention may be used with other types of medication or other injectable or deliverable substances, such as vitamins, growth hormones or the like. Moreover, embodiments of the present invention may be used with various types of medication delivery devices such as pen-type injectors, jet injectors, medication pumps, inhalers, sprays and the like. Furthermore, in other embodiments, the blood characteristic monitor may be used to monitor other characteristics, such as hormone levels, cholesterol levels or the like. In alternative embodiments, a different type of characteristic monitor may be used, such as for determining the characteristics of a urine sample, a saliva sample or the like.

Embodiments of the present invention combine medication delivery devices, such pen-type injectors or the like, with a microprocessor to accurately set and determine the dosage of a medication that is administered to the user. Moreover, the microprocessor serves to record important information concerning the medication delivery, such as the date, the time and the amount of medication administered. This information is displayed on an LCD display, or the like, for easy review by the user or doctor. This allows the user to carry one self-contained medication delivery device that does not require carrying a separate medication vial and syringes, since, for example, the vial is contained within the pen-type injector or the like. Moreover, the user does not have to carry a separate log book to record relevant and required information concerning the injection, blood characteristics, meals, exercise, unscheduled events or the like, since this information is automatically recorded by the microprocessor for later recall.

Embodiments of the present invention are portable and compact, which is essential for a person with diabetes who is required to inject insulin multiple times a day. It is especially beneficial for children with diabetes who must take the device to school (where syringes are banned) and use it under the supervision of an adult who may not be a Registered Nurse. Embodiments of the device automatically record the insulin dosage type, amount, date and time in memory. This feature is especially beneficial to the supervising health care professional, patient and parent, since they now have accurate (unalterable) records of the patients daily treatment regimen for analysis. In addition to convenience, a medication delivery device with memory provides a substantial cost savings compared to syringes and bottled insulin. Particular embodiments also include programmable daily alarms with reminder messages and a clock to assist the user in maintaining a medical regimen.

A preferred embodiment of a pen-type injector has a direct drive injection mechanism for accurate dosing and ease of use. The drive utilizes a rotatable dosage knob provided at one end of the pen-type injector. The dosage knob allows the user to accurately adjust the amount of medication or insulin that will be injected by the pen-type injector, since rotating the dosage knob limits the distance that the dosage knob can be depressed. Accuracies of 0.001 to 0.01 ccs (0.1 to 1.0 units) can be readily achieved. To inject a dose of medication, the user inserts the needle under the skin and depresses the dosage knob once as far as it will depress.

In preferred embodiments, the medication delivery device is also combined with a blood characteristic monitor that determines the level of medication, glucose or the like in a blood sample. The blood characteristic monitor uses the microprocessor in the medication delivery device (although a separate microprocessor could be used) to process the blood sample results and to store relevant information about the results. Thus, a single, all-in-one device provides medication delivery, blood characteristic monitoring, and record keeping. Therefore, a user is only required to carry a single device, and is not required to carry a large number and variety of items to comply with their medical regimen. For example, a separate medication vial, a separate medication injector, a separate blood characteristic monitor and a separate log book are not needed.

In other embodiments, a pen-type injector utilizes a disposable needle that minimizes or substantially eliminates the bleeding that may occur from administering an injection. The disposable needle includes a protective, hollow cylindrical cover that prevents the user from pushing the needle too deeply into the skin. Moreover, the hollow cylindrical cover tends to press the skin together during the administration of an injection to restrict and substantially eliminate bleeding during the injection.

In another preferred embodiment of the present invention, a portable blood monitor combines a blood characteristic monitor with a wrist watch. The blood characteristic monitor is coupled to a microprocessor to analyze blood samples and record relevant data for later recall. The wrist watch performs time keeping functions and provides alarms to notify the user when to monitor blood characteristics and when to administer injections. In particular embodiments, the portable blood monitor has a plurality of keys that allow the user to input additional information concerning injections and special events. In other embodiments, the portable blood monitor includes a data input and output port to provide the capability of programming the portable blood monitor through an external computer, such as a PC, laptop or the like, and to provide for the capability to download the stored information to an external computer for detailed review and analysis by the user or doctor.

FIGS. 1–3 show a pen-type injector 10 with a microprocessor 32 in accordance with an embodiment of the present invention. The pen-type injector 10 includes a rotatable actuator dosage knob 12, an injection housing 14, and a medication cartridge housing 16 having a view window 18. The actuator knob 12 is coupled to one end of the injection housing 14, and is also operatively coupled to an injection mechanism 20 (see FIG. 3) that is contained within the injection housing 14. The medication cartridge housing 16 is sized to hold a medication cartridge 22 (see FIG. 3) and is coupled to the other end of the injection housing 14 so that the injection mechanism 20 is operatively coupled to the medication cartridge 22. In preferred embodiments, the medication cartridge housing 16 is coupled to the injection mechanism housing 14 by threads, and the medication cartridge 22 is connected to the medication cartridge housing 16 by threads, a friction fit or the like. In particular embodiments, the medication cartridge 22 contains 1.5 ccs (150 units); however, medication cartridges containing more or less medication may be used. In preferred embodiments, the medication cartridge 22 is a Novolin® cartridge by Novo Nordisk Pharm, Inc., an insulin cartridge by Eli Lilly, Inc or any other ISO standardized cartridge.

The view window 18 of the medication cartridge housing 16 allows the user to view the interior contents of the medication cartridge 22. Thus, a user can visually determine when a medication cartridge 22 needs to be replaced with a refill medication cartridge 22, or the user can visually determine the type of medication that is currently contained in the medication cartridge housing 16.

Coupled to the other end of the medication cartridge housing 16 is a needle base 24 for holding a protective needle cover 26 and a disposable needle 28. The needle cover 26 and the disposable needle 28 are detachably coupled to the needle base 24 by threads, friction or the like. The protective needle cover 26 prevents needle pricks until an injection is to be administered. The use of a disposable needle 28 reduces the chances of spreading infections and allows the pen-type injector to be used multiple times. In preferred embodiments, the disposable needle 28 also includes a protective needle sheath 30 to further reduce the likelihood of unintended needle pricks. In particular embodiments, the pen-type injector uses a 27 gauge disposable needle 28; however, other gauges may be used.

Also attached to the injection mechanism housing 14 is a microprocessor 32, a display 34 and a clip 36. The microprocessor 32 accurately determines the dosage of the medication to be injected based upon the rotations of the actuator knob 12 by the user. The microprocessor 32 provides the dosage information to the display 34 to inform the user of the amount of medication that will be injected. In particular embodiments, the display 34 may include a set of user actuatable buttons to set various parameters in the microprocessor, such as the time, the date or the like. This allows the user to utilize the pen-type injector 10 like a clock and to set reminder alarms. The clip 36 attached to the injection mechanism housing 14 provides the capability for the pen-type injector 10 to be carried around like a traditional ball point pen. For example, the pen-type injector 10 can be carried unobtrusively in a shirt-pocket or on a clip board.

As shown in FIG. 3, the injection mechanism housing 14 also includes a start button 38. The start button 38 releases the actuator knob 12 from the position shown in FIGS. 1–2 to the released position shown in FIG. 3. The start button 38 locks the actuator knob 12 in the depressed position to prevent accidental discharges of the medication until an injection is to be administered. The start button 38 also activates the microprocessor 32 only when the microprocessor 32 is needed, and this reduces the overall power consumption characteristics of the device.

In preferred embodiments, the actuator knob 12, the injection housing 14, the medication cartridge housing 16, the needle base 24, the protective needle cover 26, and the start button 38 are formed from a plastic material. However, in alternative embodiments, some or all of these parts may be formed from metals, ceramics or other suitable materials. In preferred embodiments, the view window 18 is formed from plastic; however, glass may be used in alternative embodiments. In preferred embodiments, the display 34 is an LCD display; however, in other embodiments, the display may use fluorescent elements, LEDs, electro-luminescent LCDs or the like.

Figure 4:
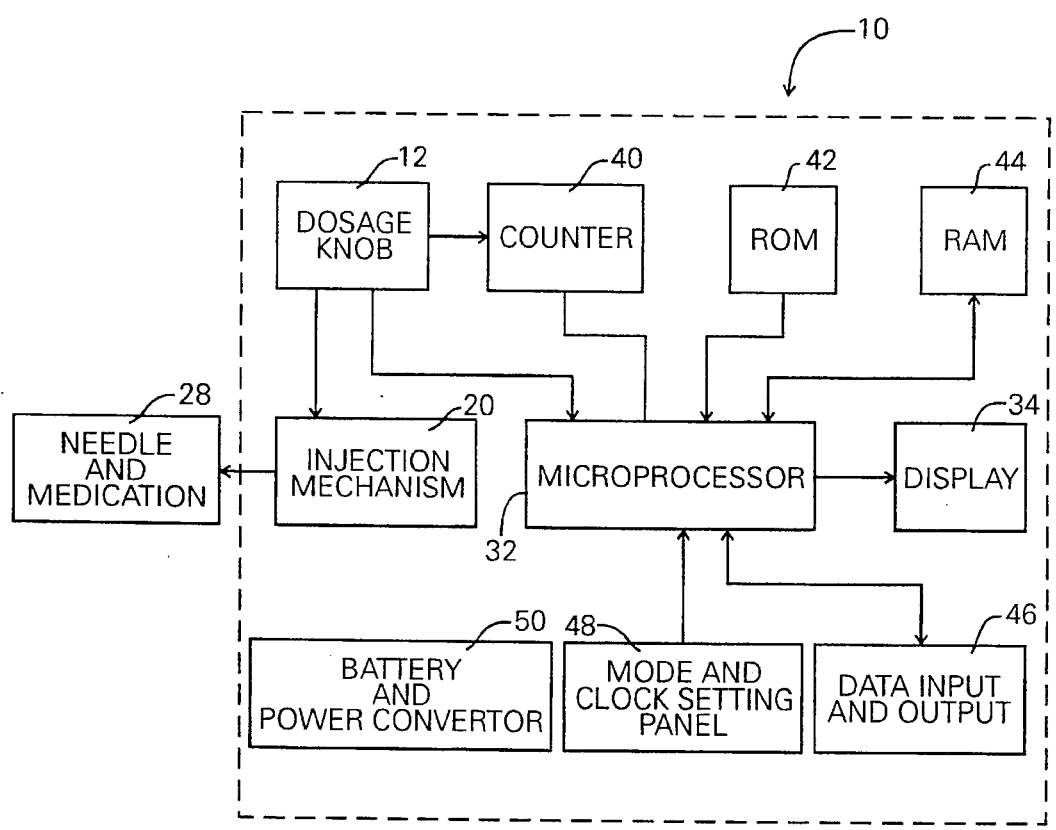
FIG. 4 is a simplified flow block diagram for the pen-type injector as shown in FIG. 1.

FIG. 4 illustrates a simplified flow block diagram of the pen-type injector 10 shown in FIGS. 1–3. The actuator dosage knob 12 is rotated to adjust the injection mechanism 20 and set the dosage of the medication to be injected by the disposable needle 28. In preferred embodiments, the actuator knob 12 can be rotated in two directions to both increase or decrease the dosage level. The actuator knob 12 is coupled to a counter 40 that keeps track of the incremental rotations of the actuator knob 12 and injection mechanism 20. In particular embodiments, the counter 40 is an electronic counter, and in preferred embodiments the electronic counter is bi-directional and can increment and decrement the dosage level. The counter 40 is coupled to the microprocessor 32 to provide the current count in the counter 40 to the microprocessor 32. The current count from the counter 40 is converted into a value equal to the dosage of the medication that will be administered by an injection. The actuator knob 12 is also coupled directly to the microprocessor 32 to activate the microprocessor 32. Thus, when the start button 38 releases the actuator knob 12, the microprocessor 32 is prepared to store relevant information concerning the injection. For instance, the microprocessor 32 will store, the time, the date and the amount of medication injected by the user.

The microprocessor 32 is coupled to a ROM 42 and a RAM 44. In preferred embodiments, the ROM 42 is an EPROM and the RAM 44 is a static RAM; however, other comparable memory storage components such as dynamic RAM, non-static RAM, rewritable ROMs or the like may be used. The ROM 42 stores the programs used by the microprocessor 32 to determine various parameters, such as the amount of medication to be injected based upon the count from the counter, the date and the time, and how to report information to the user. The RAM 44 is used by the microprocessor 32 to store information about the injection for later recall by the user or the doctor. For example, a user or doctor can transcribe the stored information at a later time to determine compliance with the medical regimen. This is accomplished by downloading the information to the display 34 and then transcribing all of the stored records at one time as they appear on the display 34.

In preferred embodiments, the microprocessor 32 is coupled to a data input and output (I/O) port 46, and the user can download the stored information to an external computer (not shown) through the data I/O port 46 to produce a report such as shown in FIG. 24(c). The data I/O port 46 is capable of transferring data in both directions so that updated program instructions or reminder alarms can be set by the user or doctor. In preferred embodiments, the I/O port 46 uses infrared (IR) technology or bar code readers. However, in alternative embodiments, the I/O port 46 may use other data transfer technologies such as cables, fiber optics, radio waves or the like.

Also coupled to the microprocessor 32 is a mode and clock setting panel 48 that provides the user with the capability to store additional information, set the date and the time, or set alarms to indicate when to take the next injection. The panel 48 is used in conjunction with the display 34 to access the various modes and alarms utilizing methods typically employed to set the time on an LCD watch or the like.

The pen-type injector 10 also includes a self contained battery and power convertor 50. The battery is a small watch type battery, or in preferred embodiments, the battery is a lithium battery capable of providing power for up to 5 years.

Operation of the embodiment shown in FIGS. 1–4 is relatively simple. The user prepares the pen-type injector 10 by depressing the start button 38 to activate the microprocessor 32. If a new medication cartridge 22 is required, the user unscrews the medication cartridge housing 16 from the injection mechanism housing 14, and couples a pre-filled medication cartridge 22 to the injection mechanism 20 and the injection mechanism housing 14. Once the medication cartridge 22 is attached, the user rescrews the medication cartridge housing 16 onto the injection mechanism housing 14. Next, the user removes the protective needle cover 26 and attaches a disposable needle 28 to the needle base 24. The user then holds the pen-type injector 10 with the disposable needle 28 pointing upward and rotates the actuator knob 12 to set a small amount of medication (typically 2–4 units). The user then depresses the actuator knob 12 to eliminate the small amount of medication and remove the air from the disposable needle 28. The user may also use a recall and delete function to delete the air removing injection from memory to prevent it from being stored with the other stored data. Alternatively, the user can mark this entry as an air removal injection, once it is stored in the memory. Depression of the actuator knob 12 delivers the set amount of medication. The system then remains on for 60 seconds (although longer or shorter times may be used) after the actuator knob 12 has been depressed so that the user can delete the most recent entry such as an air shot. After 60 seconds (although longer or shorter times may be used), the pen-type injector powers itself down. Finally, the user reattaches the protective needle cover 26 to prevent inadvertent needle pricks or damage to the disposable needle 28.

To give an injection with the pen-type injector 10, the user removes the protective needle cover 26 and, if present, the protective needle sheath 30. The actuator knob 12 is released and the microprocessor 32 is activated by depressing the start button 38. In preferred embodiments, when activated, the microprocessor 32 displays the time and the amount of the last injection on the display 34 in an alternating sequence for 5 seconds (although longer or shorter periods may be used) to remind the user of the last injection event. This substantially reduces the chance of "double dosing" (i.e., taking too much medication). After the reminder display, the pen-type injector 10 automatically zeros itself so that the user can dial in and set the dosage by rotating the actuator knob 12 in one direction (typically clockwise) until the desired amount of the medication to be injected is displayed on the display 34. In particular embodiments, the display 34 changes in real time, and in preferred embodiments, an audible click or beep is heard as the user rotates the actuator knob 12. Also in preferred embodiments, each click represents an incremental change in the dosage selected (i.e., 0.1, 0.25, 0.5 or 1.0 units). In bi-directional models, the user can increase or decrease the amount of medication to be injected. However, the microprocessor 32 will not allow the user to set a dosage below zero or to select a dosage larger than the amount of medication remaining in the medication cartridge 22. If any incorrect dosage is selected or any step in the injection process is not properly performed, an error message will be displayed on the display 34.

In further embodiments, if an injection or other function is not performed within a predetermined period of time (e.g., 1 minute or the like), the pen-type injector shuts down to conserve power in a "sleep mode." Activation of a function button or turning the dosage knob 12 will reactivate the pen-type injector 10.

After the dosage is selected, the user chooses an injection site, pushes the disposable needle 28 under the skin and depresses the actuator knob 12 down as far as it will go. The actuator knob 12 automatically locks in the depressed position when the actuator is depressed completely and the injection is completed. When the actuator knob 12 is depressed, the microprocessor 32 stores the injection event in the RAM 44 by the date, the time and the amount of injected medication. When the user returns home or after a certain number of injections have been administered, the user can activate the microprocessor 32 with the mode and clock setting panel 48 to review the recorded data as it is displayed on the display 34. The patient can then transcribe this information in a separate log book if desired. When the user visits the doctor, the doctor can download all the stored injection information into an external computer via the data I/O port 46 to produce a report similar to the one illustrated in FIG. 24(c). The doctor can then review the data to spot trends and determine compliance with the medical regimen. If required, the doctor can update the program instructions in the pen-type injector 10 via the data I/O port 46 to provide reminder alarms at various times.

Figure 13:
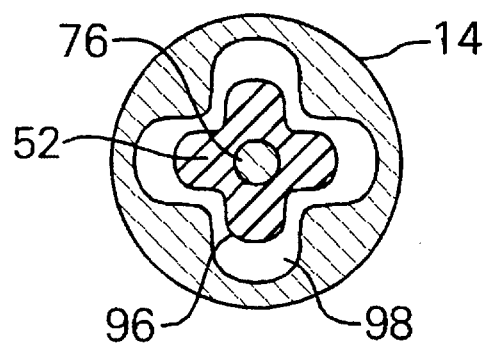
FIG. 13 is a cross-sectional view of the pen-type injector as shown along the line 13—13 in FIG. 6.

FIGS. 5 and 6 show detailed cross-sectional views of a preferred embodiment of a direct drive injection mechanism 20 as shown along the line 5—5 in FIG. 2. FIGS. 7(a)–7(i) show exploded views and details of the direct drive mechanism 20. FIGS. 8–12 show various views that detail the drive mechanism 20 shown in FIGS. 5 and 6. FIG. 13 is a cross-sectional view of the drive mechanism 20 along the line 13—13 shown in FIG. 6. The drive mechanism 20 includes a dosage knob drive shaft 52, a tension spring 54, a lock nut 56, a display seat 58, an offset camshaft 60, an electronics mount 62, a ratchet spring 64, a ratchet collar 66, a drive calibrator 68, a ratchet gear 70, a synchronizer spring 72, a stationary synchronizer 74, a threaded drive shaft 76, a plunger 78, an end cap 80, a medication cartridge tensioner and synchronizer 82, and a medication cartridge plunger 84 that are coupled as shown in FIGS. 5–12.

Figure 7A:
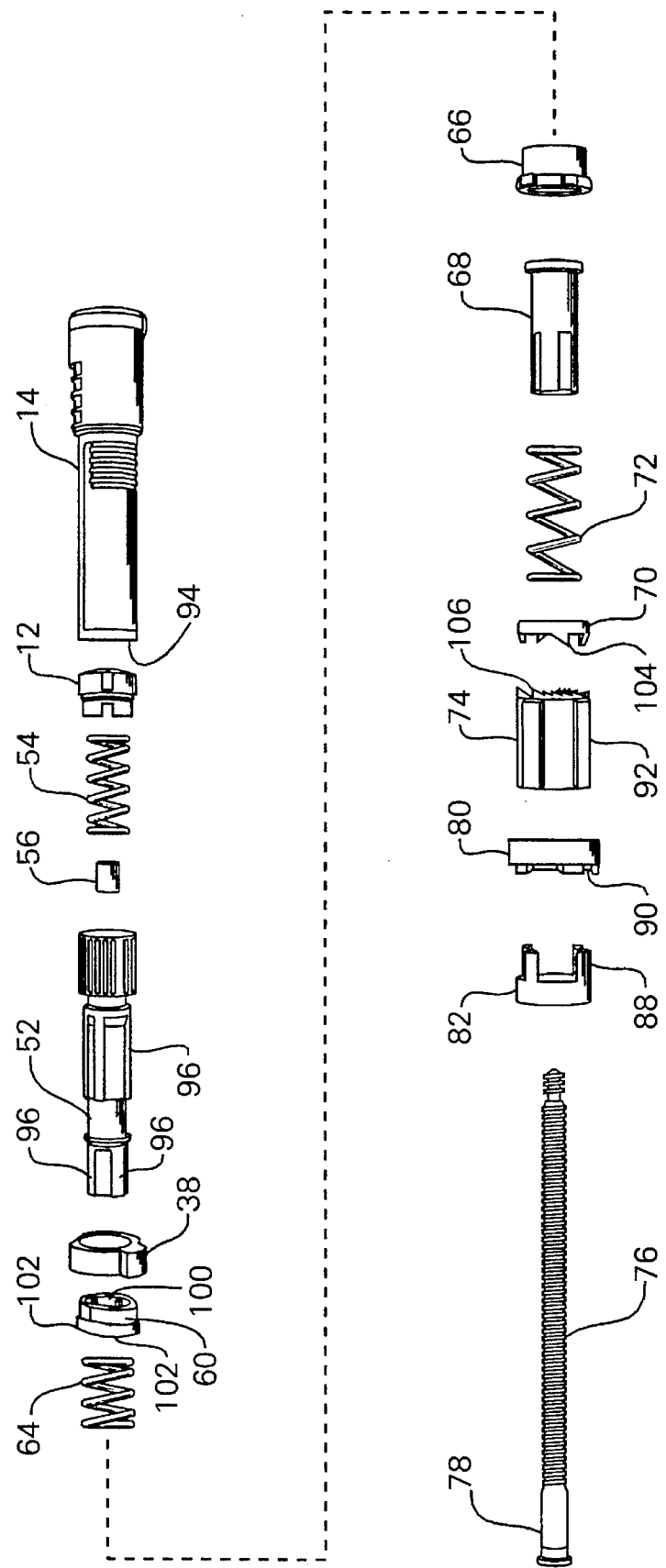
Figure 8:
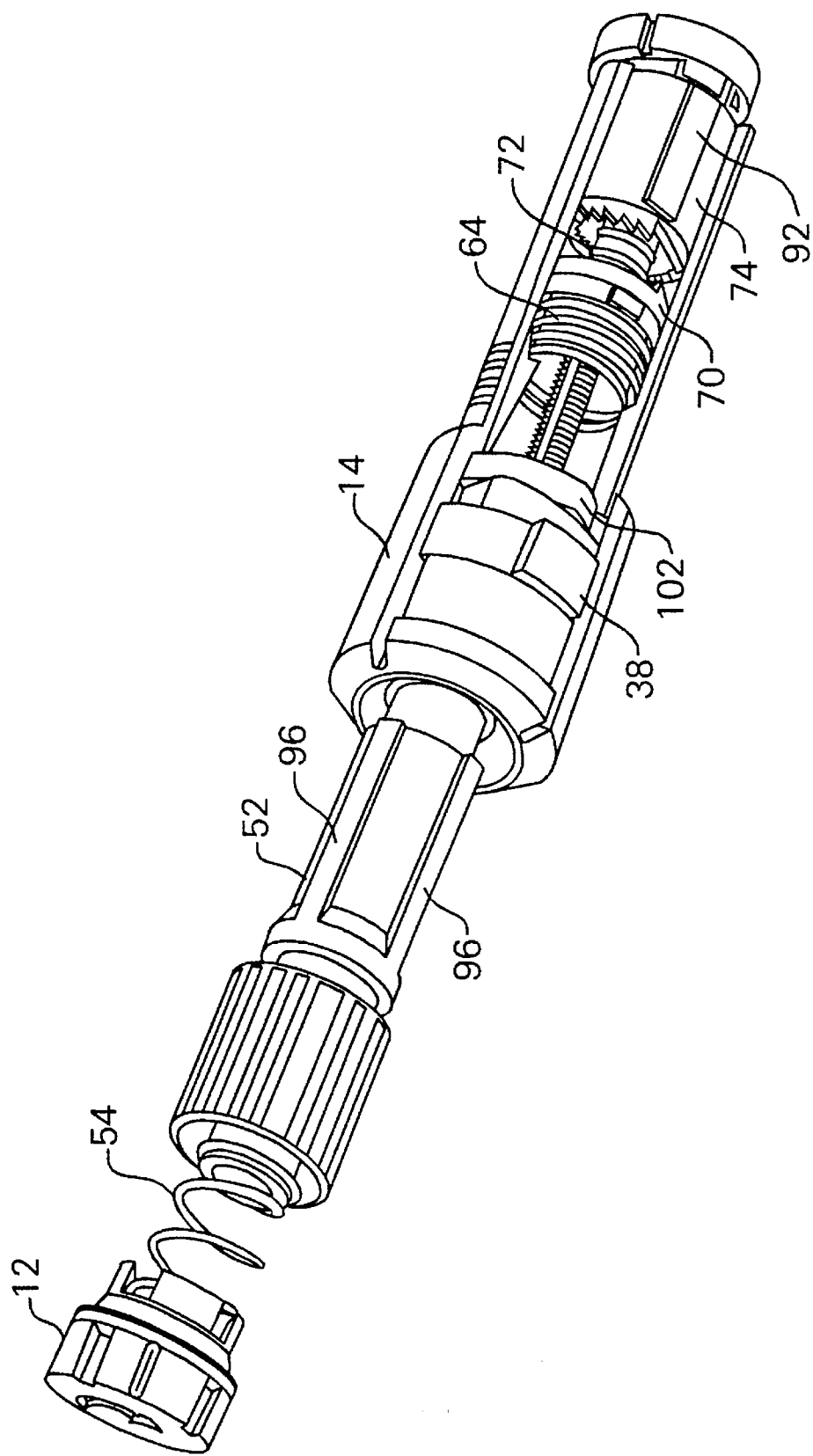
FIGS. 8–12 show various views of the drive mechanism in accordance with an embodiment of the present invention.
Figure 9:
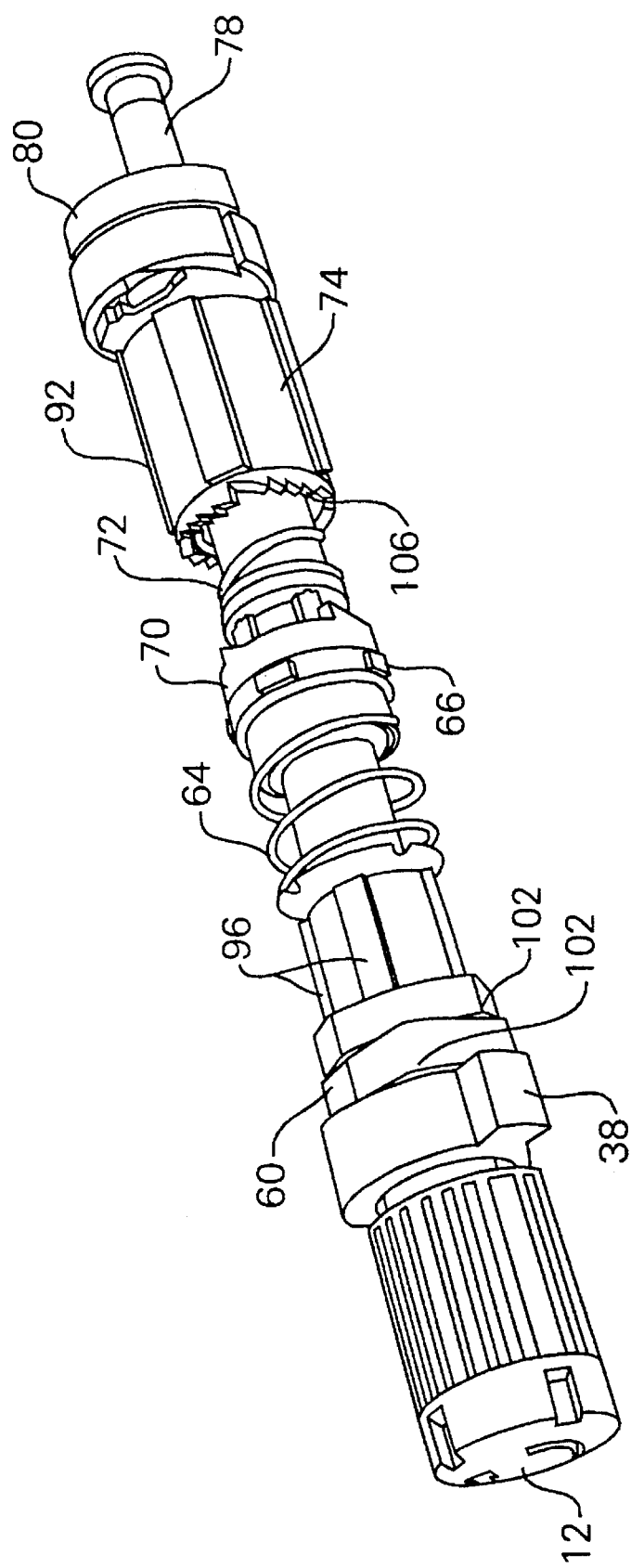
Figure 10:
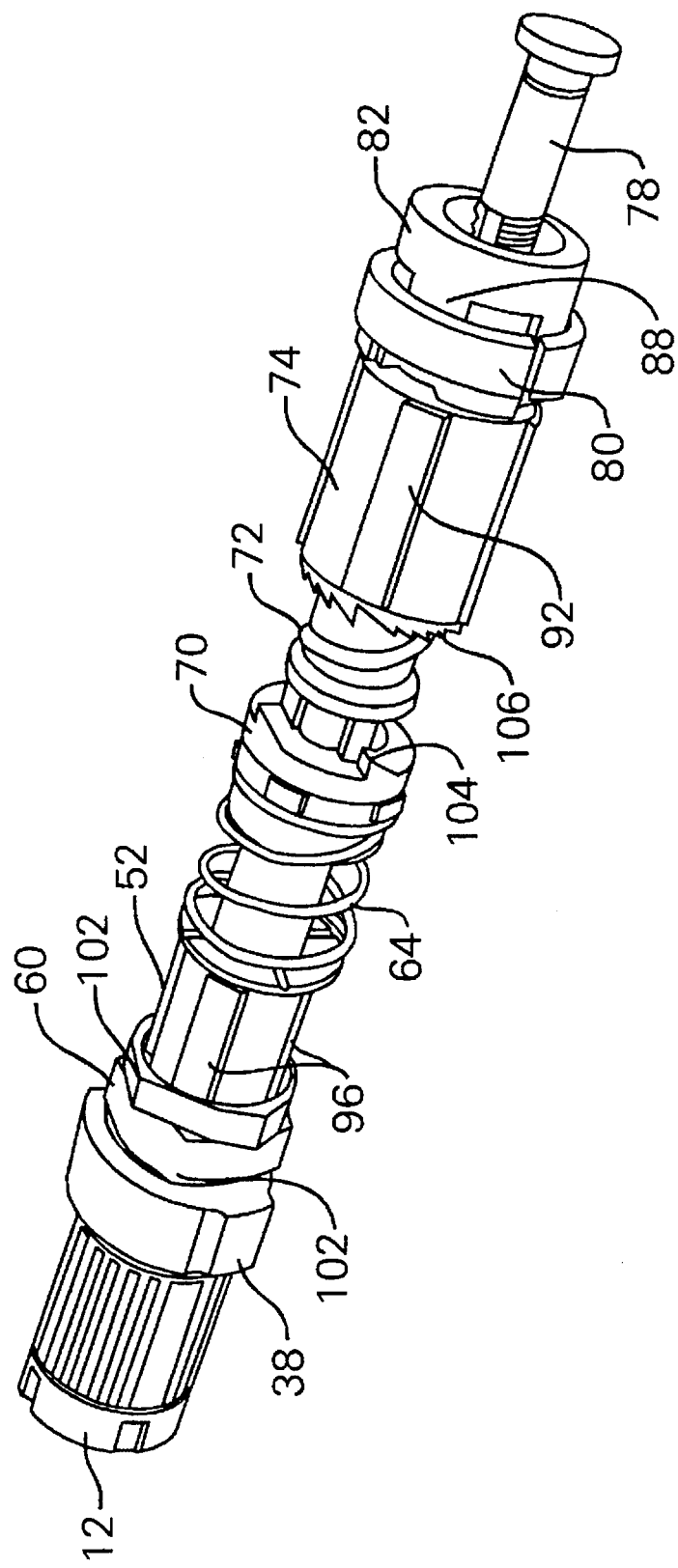
Figure 11:
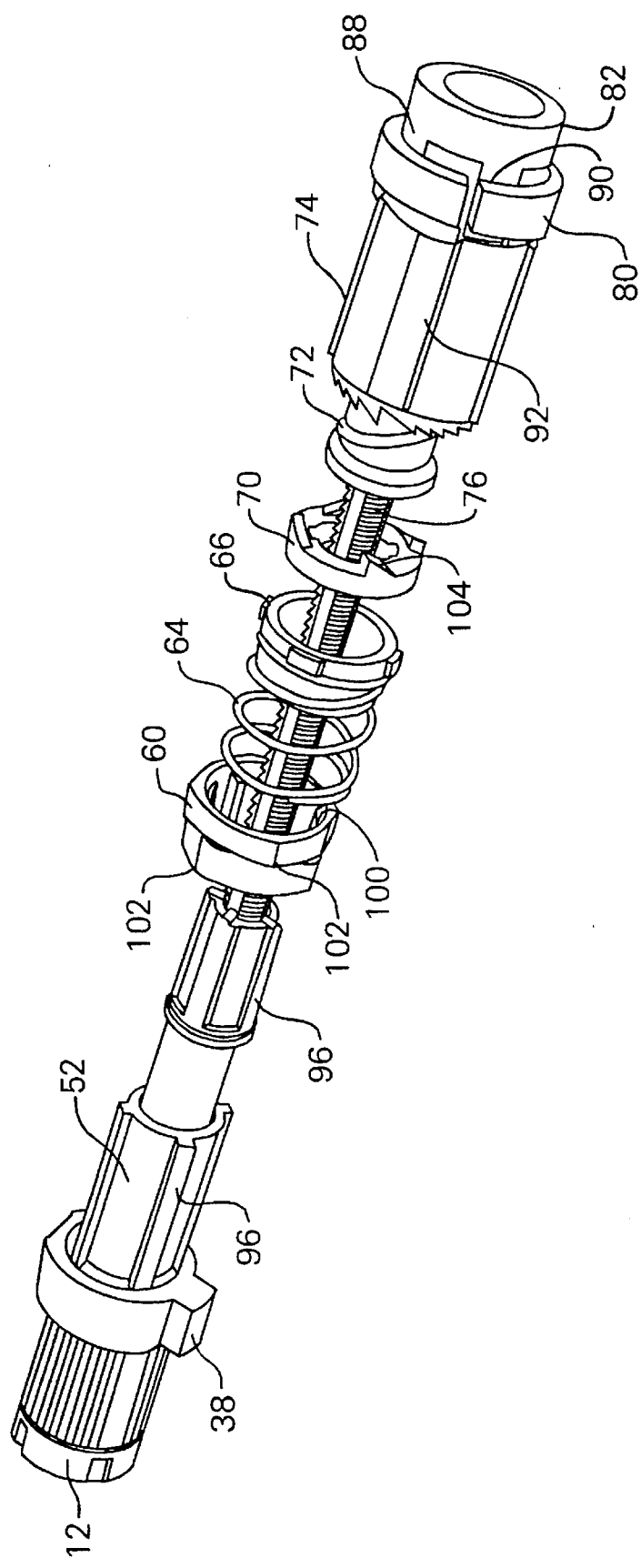
Figure 12:
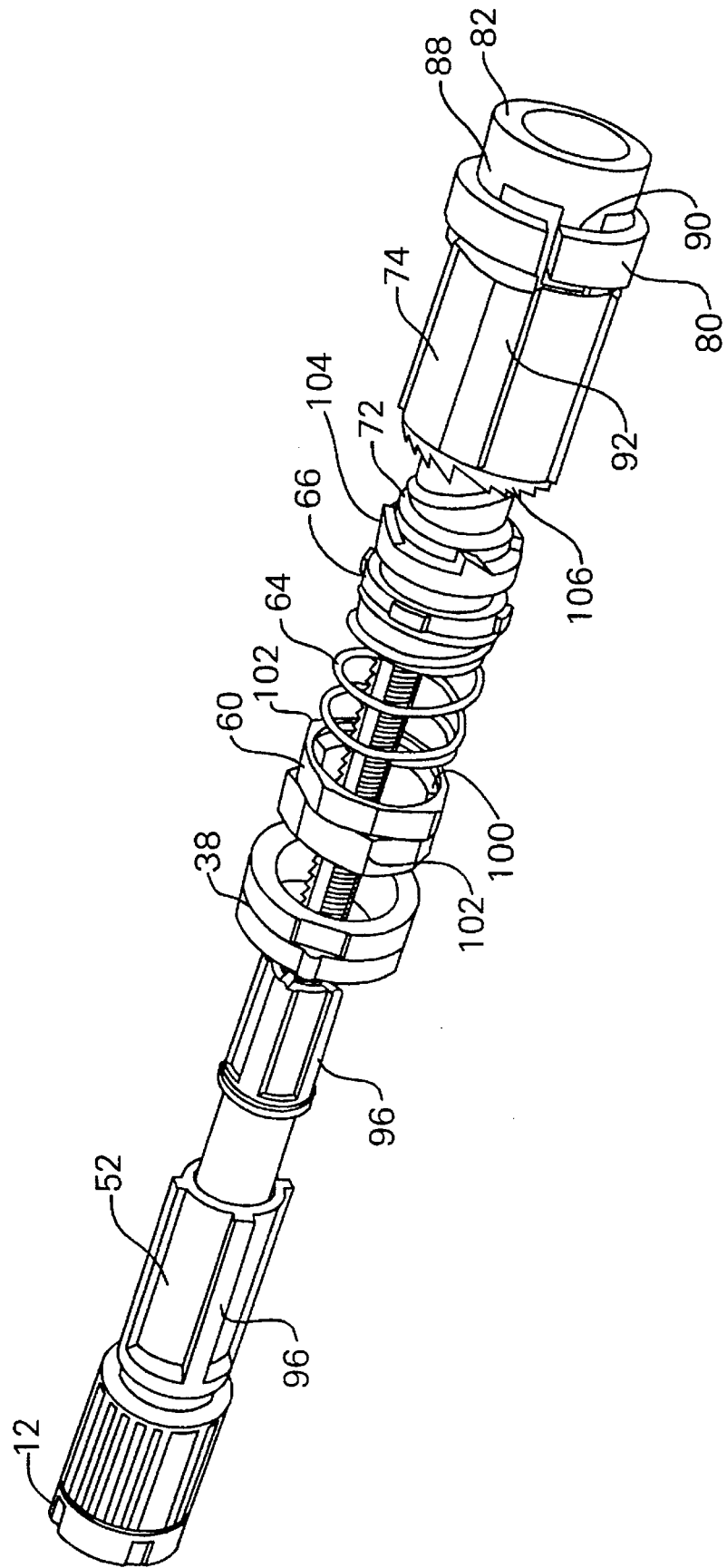

The dosage knob drive shaft 52 is coupled to a splined dosage actuator 53 by a splined retainer 55 (see FIGS. 7(a) and 7(d)). The splines 96 of the dosage knob drive shaft 52 are timed to the splines 96A of the splined dosage actuator 53 at a 45 degree rotational offset (alternative embodiments may use other angular rotational offsets). The offset is referenced by the pre-determined fixed location of the splined retainer 55 during assembly to the tubular end of the drive shaft 52. The dosage knob drive shaft 52, the dosage actuator 53, the splined retainer 55 and the dosage actuator knob 12 form a sub-assembly. The sub-assembly is coupled to the threaded drive shaft 76 by a left-handed threaded locknut 56. The threaded drive shaft 76 has a double keyway that runs the entire length of the threads on the threaded drive shaft 76 to allow the drive shaft 76 to move laterally in a keywayed bore 57 (see FIGS. 5, 6 and 7(e)–7(i)) of the dosage knob drive shaft 52 along the centerline axis of the sub-assembly when the dosage actuator 53 is rotated in a clockwise or counter-clockwise direction for the purpose of selecting a dosage setting. The double internal keyway in the splined end of the bore of the dosage knob drive shaft 52 is used to hold the threaded drive shaft 76 in a fixed position that prevents the threaded drive shaft 76 from rotating within the sub-assembly. The left-handed threaded locknut 56 is a retainer that prevents the threaded drive shaft 76 from traveling past a stop 59 located in the end of the dosage knob drive shaft 52 (see FIG. 7(e)). The threaded locknut 56 also determines the end of the stroke for the threaded drive shaft 76, which corresponds with a pre-determined position of the threaded drive shaft 76 to signify an empty medication cartridge.

The start button 38 is also coupled to the dosage actuator 53 to maintain the dosage actuator sub-assembly in a depressed position when the pen-type injector 10 is not being used, and to release the spring tensioned dosage actuator 53 and activate the microprocessor 32 when the pen-type injector 10 is to be used for an injection. Contained within the internal housing of the dosage actuator sub-assembly is a tension spring 54 that is securely attached to the interior of the sub-assembly by the actuator knob 12. The purpose of the spring 54 is to hold the sub-assembly in a pre-determined tension to provide drive shaft dampening from the hydraulic loads produced during the injection cycle. All free tolerances in the dosage actuator sub-assembly are taken up by the tension spring 54 to maintain the sub-assembly in a stable configuration and to help insure injection dosage accuracy. When the starter button 38 is depressed, the synchronizer spring 72 displaces the entire dosage actuator sub-assembly along with the threaded drive shaft 76 and the drive calibrator 68 to move them into the activated position to select a dosage and inject the selected dosage of medication. Tension spring 54 and ratchet spring 64 provide shock damping for the dosage actuator sub-assembly, when it is ejected to and stopped at the activated position. The synchronizer spring 72 also facilitates maintaining the plunger 78 in a proper position with respect to the insulin cartridge plunger 84 when the pen-type injector 10 is not being used, so as to minimize the effects of fluid expansion or contraction that could draw air into the insulin cartridge 22 during storage.

The dosage knob drive shaft 52 that is assembled with the dosage actuator 53 has splines 96 which, when the dosage actuator 53 is in the depressed position, are locked in corresponding spline slots 98 of the injection mechanism housing 14 to prevent the dosage actuator 53, the splined retainer 55, the dosage actuator knob 12, the dosage knob drive shaft 52 and the threaded drive shaft 76 from being rotated. When the dosage actuator 53 of the dosage knob sub-assembly is released by the start button 38, the dosage actuator 53, the dosage actuator knob 12 and the dosage drive shaft 52 move in a direction away from the medication cartridge 22. The splines 96 then slide clear of the spline slots 98 so that the dosage actuator 53, the dosage actuator knob 12, the dosage knob drive shaft 52 and the threaded drive shaft 76 can be rotated as a single unit. This allows the relative positioning of the threaded drive calibrator 68 and the threaded drive shaft 76 to be adjusted, resulting in the drive calibrator 68 being advanced or retarded in position to adjust the dosage of medication that will be injected by the pen-type injector 10.

The splines 96A of the dosage actuator 53 are coupled to internal spline slots 100 of the offset cam collar 60 which is coupled to the counter 40 mounted on the electronics mount 62. The offset cam collar 60 has cam lobes 102 that are in operative contact with rocker switches (contact switches or the like) on the counter 40. When the dosage actuator 53 and dosage actuator knob 12 are rotated, the dosage knob drive shaft 52, the splined retainer 55, and the dosage actuator knob 12 sub-assembly rotate the offset camshaft 60 and the cam lobes 102 to actuate the rocker switches (not shown) to increment the counter 40 by one count per each predetermined angle of rotation of the dosage actuator 53. The rotation of the dosage knob actuator knob 12 sub-assembly also changes the axial positioning of the threaded drive calibrator 68 relative to the threaded drive shaft 76. This causes the drive calibrator 68 to advance or retard in position relative to the threaded drive shaft 76 depending on the direction of rotation of the dosage actuator 53 and dosage actuator 12 to adjust the dosage of the medication to be injected. In preferred embodiments, the pre-determined angle of rotation is 90 degrees (although larger or smaller angles may be used).

FIG. 7(c) illustrates an alternative to the offset camshaft 60 and cam lobes 102 that are operatively coupled with the rocker switches (not shown) on the counter 40. The alternative is a round drum 60' having a plurality of thin bar code lines 102' and thick bar code lines 102" that are read by the counter through an optical sensor and light pipe (not shown). The lines 102' and 102" are grouped in pairs of one thin line 102' next to one thick line 102". The pairs are spaced at predetermined angles around the round drum 60' to represent increments to increase or decrease the dosage amount to be injected. In preferred embodiments, the pairs of lines are spaced at 90° increments around the round drum 60' (although larger or smaller increments may be used). In particular embodiments, the optical sensor senses one direction of rotation of the round drum 60' by detecting a thin line 102' followed by a thick line 102" and then increments the counter 40 by one for each set of detected lines. Conversely, if the sensor detects a thick line 102" followed by a thin line 102', it determines that the rotation is in the opposite direction and decrements the counter 40 by one. In alternative embodiments, the lines may be a reflective material, rather than dark bar code lines. In further alternatives, the sensor may use infrared (IR) radiation or may use optical sensors that do not require light pipes.

The display seat 58 is adapted to hold the display 34 and the microprocessor 32. The microprocessor 32 is coupled to the counter 40 that is mounted on the electronics mount 62 to determine the dosage of medication to be injected based upon the value in the counter 40. The display seat 58 may also be used to hold the clip 36 to allow the pen-type injector 10 to be carried like a pen.

The ratchet spring 64 is permanently attached to the interior of the injection mechanism housing 14. The ratchet spring 64 applies pressure to the ratchet collar 66 which in turn applies pressure to the ratchet gear 70. The ratchet gear 70 has teeth 104 that mate correspondingly with teeth 106 on the stationary synchronizer 74. The synchronizer spring 72 applies a counter-pressure on the stationary synchronizer 74 to maintain the ratchet gear 70 and the stationary synchronizer 74 in contact with each other. Thus, when the actuator knob 12 is rotated, a ratchet noise is produced as the ratchet gear 70 is rotated relative to the stationary synchronizer 74. Removal of the medication cartridge 22 reduces the pressure on synchronizer spring 72 so that the corresponding teeth 104 and 106 of the ratchet gear 70 and the stationary synchronizer 74 are disengaged. When the teeth 104 and 106 are disengaged, the actuator knob 12 can be rotated easily with minimal resistance, and the threaded drive shaft 76 can be withdrawn without resistance from the ratchet gear 70.

The stationary synchronizer 74 also has splines 92 which are coupled to corresponding spline slots 94 in the injection mechanism housing 14 to prevent the stationary synchronizer 74 from rotating. However, the splines 92 are slidably coupled to the spline slots 94 so that the stationary synchronizer can slide back and forth within the injection mechanism housing 14. This allows the medication cartridge 22 to increase the tension of the synchronizer spring 72 when the medication cartridge 22 is seated, and this increased tension causes the teeth 104 and 106 to engage.

FIGS. 7(a), 7(d)–(i) and 8–12 illustrate a drive mechanism utilizing a mono-directional ratchet gear 70 and a corresponding mono-directional stationary synchronizer 74. The teeth 104 and 106 on the ratchet gear 70 and the synchronizer 74, respectively are shaped to permit setting the dosage in only a single direction. Thus, if a user goes past the required dosage, they must either completely reset the pen or they must eject the currently set dosage. FIG. 7(b) illustrates an alternative bi-directional ratchet gear 70' and a corresponding bi-directional stationary synchronizer 74' having teeth 104' and 106', respectively. The shape of the teeth 104' and 106' are symmetrical, as opposed to the right angular teeth 104 and 106 on the gear 70 and synchronizer 74, to permit the dosage set by the counter 40 and displayed on the display 34 to be increased and decreased. Thus, users can correct the set dosage if they go past the desired dosage amount, without having to reset the pen or ejecting the incorrectly set dosage.

The drive calibrator 68 is threaded onto the threaded drive shaft 76 to determine the minimum and maximum positions in which the threaded drive shaft 76 can be moved to inject medication from the medication cartridge 22. The drive calibrator 68 also performs as a rotational reference point to keep track of the incremental movement of the threaded drive shaft 76 so that the dosage of medication injected by the pen-type injector can be accurately determined. An end of the drive calibrator 68 has splines 88 that engage corresponding spline slots 90 in the end cap 80 to hold the drive calibrator 68 in a rotationally fixed position. The other side of the end cap 80 is coupled to the medication cartridge tensioner and synchronizer 82 which is used to secure a medication cartridge 22 to the injection housing 14. The threaded drive shaft 76 is coupled to the medication cartridge plunger 84 to inject medication in the medication cartridge 22 when the actuator knob 12 is depressed.

The illustrated direct drive mechanism only requires a single complete depression of the actuator knob 12 to inject different set amounts of medication. The illustrated direct drive allows the user to accurately set various dosage values to be injected. The drive mechanism 20 is capable of providing dosage accuracies of between 0.1 to 1.0 unit increments. However, other dosage increments may be used. Moreover, in alternative embodiments, other suitable drive mechanisms can be used by the pen-type injector such as those disclosed in U.S. Pat. No. 5,114,406 issued May 19, 1992; U.S. Pat. No 5,226,895 issued Jul. 13, 1993; and U.S. Pat. No. 5,279,585 issued Jan. 18, 1994.

Figure 14:
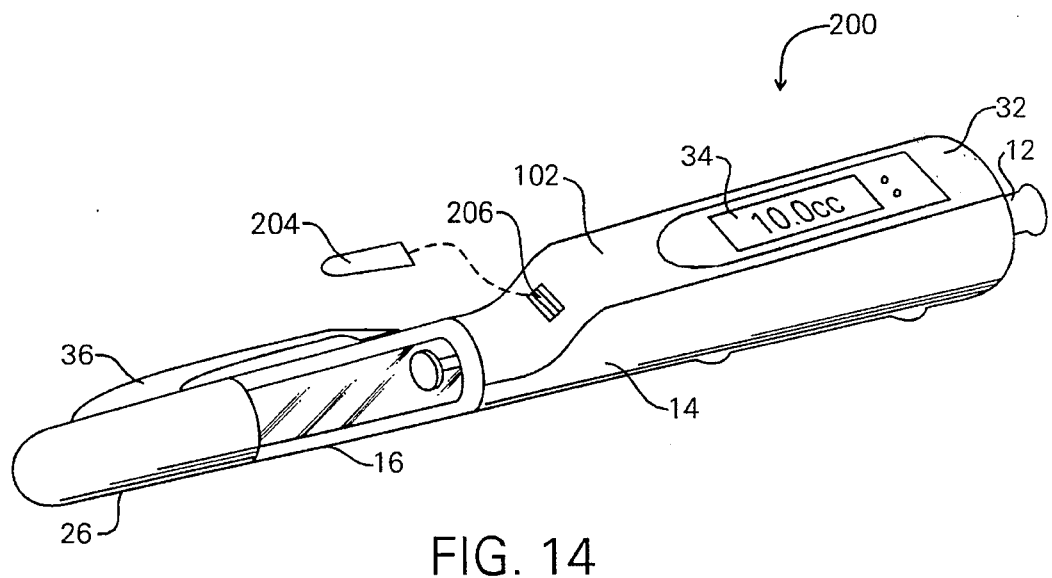
FIG. 14 is a perspective view of a pen-type injector that includes a blood characteristic monitor in accordance with an embodiment of the present invention.
Figure 15:
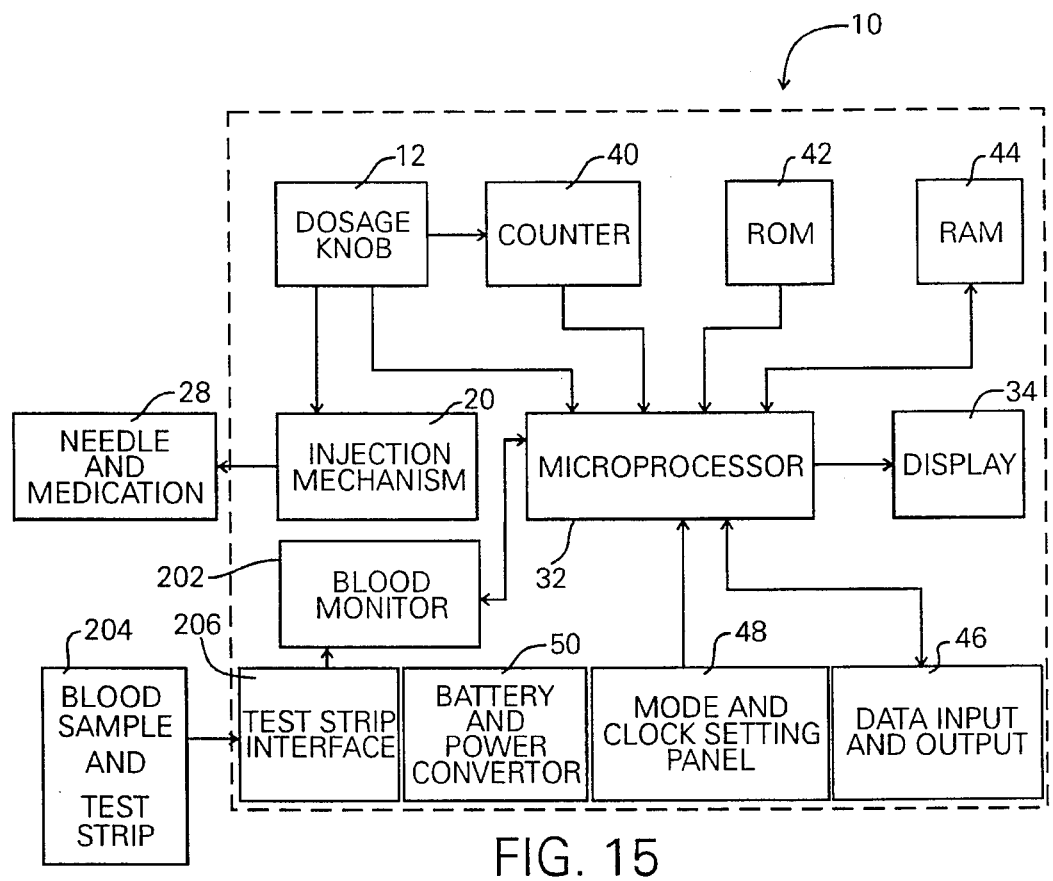
FIG. 15 is a simplified flow block diagram for the pen-type injector with a blood characteristic monitor as shown in FIG. 14.

A pen-type injector 200 in accordance with an embodiment of the present invention is shown in FIGS. 14 and 15. The pen-type injector includes a blood characteristic monitor 202, such as a glucose meter or the like, coupled to the injection mechanism housing 14. This pen-type injector 200, also includes a rotatable actuator knob 12, a medication cartridge housing 16 and a protective needle cover 26 such as those discussed above with respect to the pen-type injector 10. Instead of a window 18, the medication cartridge housing 16 is transparent to allow easy viewing of the medication cartridge 22. Moreover, the clip 36 is located on the protective needle cover 26 rather than the injection mechanism housing 14. The pen-type injector 200 also uses a microprocessor 32 and a display 34. However, in preferred embodiments the display is larger than in the previous embodiment to display more information, and both the display and the microprocessor 32 are coupled to the blood characteristic monitor 202. The pen-type injector 200 with the blood characteristic monitor 202 allows the user to use a single, all-in-one device that keeps records, injects medication, and determines characteristics of a blood sample, and that can be used to produce reports similar to those shown in FIGS. 24(a)–24(d).

FIG. 15 is a simplified block diagram of the pen-type injector 200 with a blood characteristic monitor 202. The operation of the injection mechanisms and the related components is the same as described above in the previous embodiment. In the pen-type injector 202 the ROM 42 now stores additional programs to operate and control the blood characteristic monitor 202. Moreover, the RAM 44 also stores results obtained from the blood characteristic monitor 202. As shown in FIG. 14, a test strip 204 for holding a blood sample is inserted into the test strip interface 206. This activates the blood characteristic monitor 202 and the microprocessor 32. The blood characteristic monitor 202 analyzes the blood characteristics and sends the analysis results to the microprocessor 32, which displays the results on the display 34 and stores the results in the RAM 44 for later review.

In particular embodiments, the blood characteristic monitor 202 tests for the level of glucose in the blood. Preferably, the blood characteristic monitor 202 uses electro-chemical sensor technology (i.e., the blood sample reacts with a chemical upon the application of an electrical current). The blood characteristic monitor 202 is periodically calibrated by a reusable code strip. To perform the analysis, the blood characteristic monitor utilizes a disposable (one time use) test strip 204. The test strip 204 utilizes capillary action at the end of the test strip to draw in a small amount of blood (typically 3 micro-liters) into a reaction chamber (not shown) in the test strip interface 206 of the blood characteristic monitor 202. When sufficient blood has been drawn into the reaction chamber, the test sequence begins and a blood glucose reading is displayed on the display 34 in approximately 60 seconds from the start of the testing sequence. In preferred embodiments, the blood characteristic monitor 202 provides blood glucose level results from 40–500 mg/dl (2.2–27.8 mmol/L); however, other ranges such as 20–600 mg/dl or the like may be used.

Operation of the blood characteristic monitor 202 is relatively simple. The operator fully inserts a test strip 204 into the test strip interface 206. This turns on the microprocessor 32 and the blood characteristic monitor 202. In preferred embodiments, the blood analysis mode is activated and the microprocessor 32 causes the display 34 to display the previous test result and the time of the last test event. The previous time and results are alternately flashed for 5 seconds (although longer or shorter times can be used). The user then places a blood sample (usually from a finger) on the end of the inserted test strip 204, and the capillary action in the test strip 204 draws the sample into the reaction chamber of the test strip interface 206. In preferred embodiments, the blood characteristic monitor 202 beeps, or provides some other audible indication, when a sufficient sample has been drawn into the reaction chamber. After the beep, the test is conducted and is typically completed in about 60 seconds. Once the test is completed, the results are displayed on the display 34 and simultaneously stored by the microprocessor 32 in the RAM 44 for later recall. Removal of the test strip 204 automatically turns off the blood characteristic monitor 202 and the microprocessor 32. If the user fails to remove the test strip 204, the microprocessor 32 sounds an alarm, and both the blood characteristic monitor 202 and the microprocessor 32 automatically turn off after 1 minute (although other time periods may be used). In alternative embodiments, other blood characteristic monitors may be used, such as a colormetric blood glucose meter, a dry membrane chemical reaction monitor or the like. Preferred embodiments of the present invention utilize blood characteristic monitors that use electro-chemical sensor techniques developed by Matsushita Electronics of Japan and distributed by Miles Laboratories, Inc. However, alternative embodiments, may utilize a dry chemical sensor with an electro-chemical membrane by either Boehringer Manheim Corp of Indianapolis, Ind. or MediSense of Cambridge Mass.

Figure 16A:
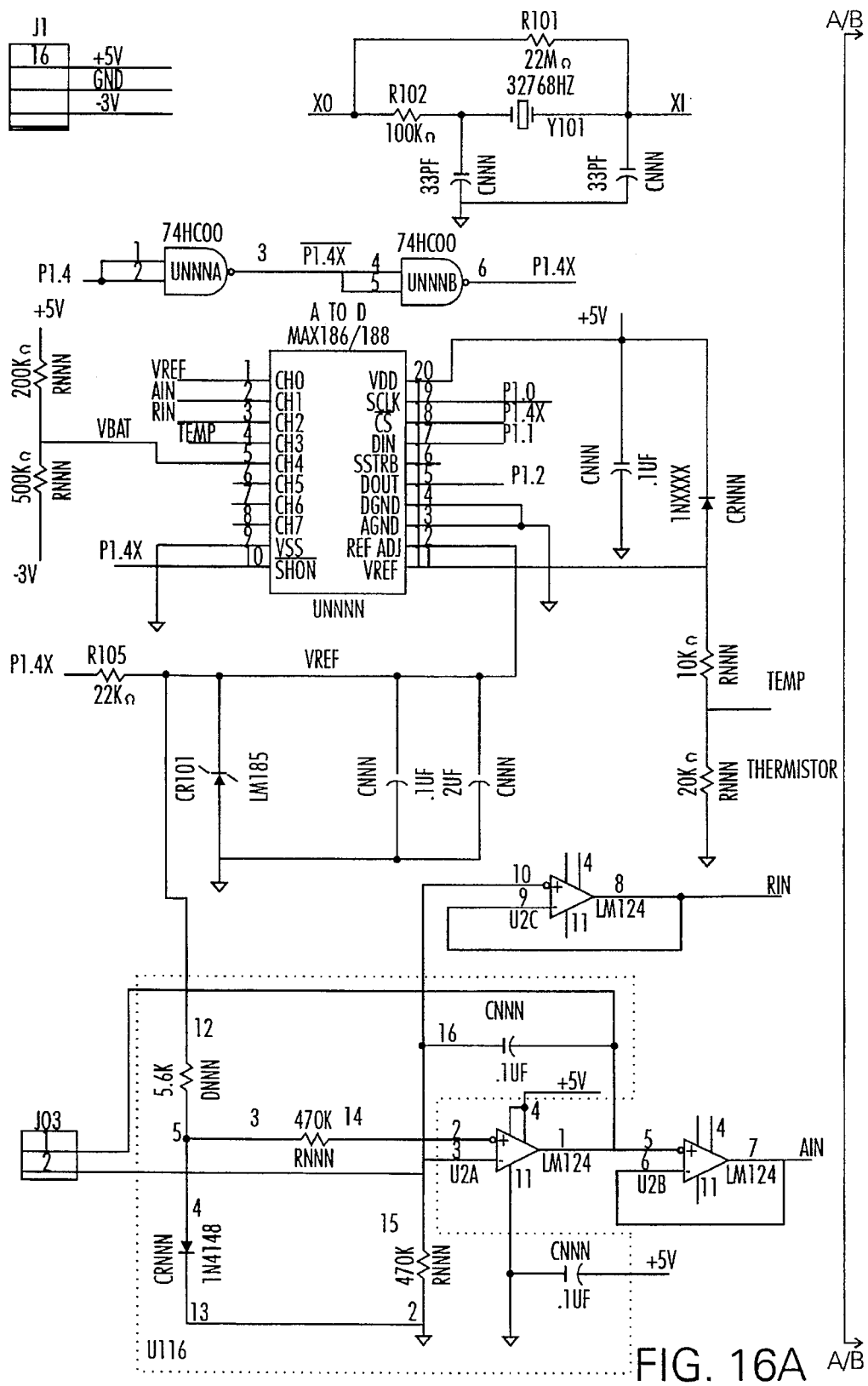
FIGS. 16A–16B are a circuit schematics for the pen-type injector with a blood characteristic monitor shown in FIGS. 14 and 15.
Figure 16B:
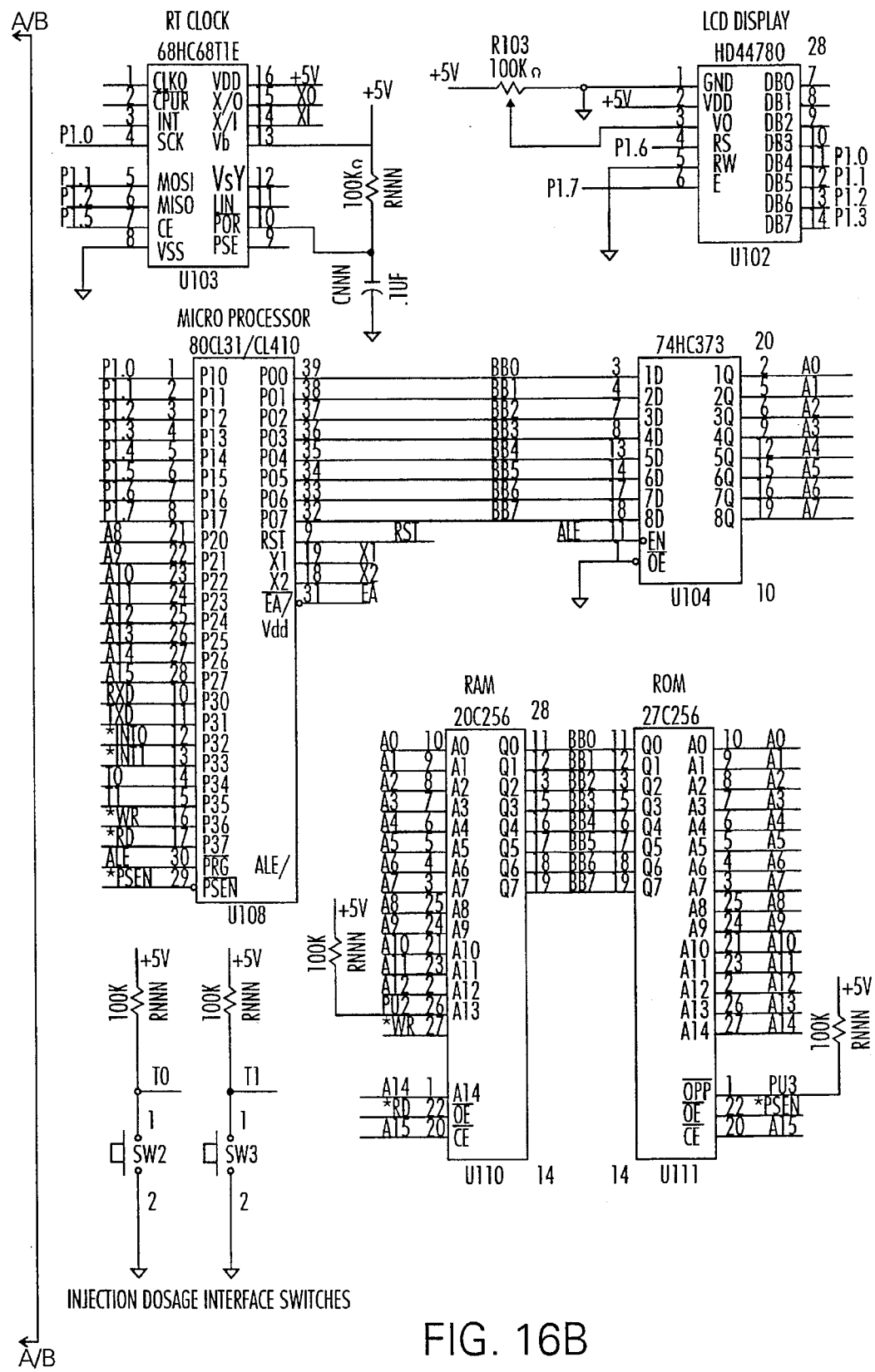

FIGS. 16A–16B are a circuit schematic showing preferred embodiments of particular circuits used in the pen-type injector 200 with a blood characteristic monitor 202. However, alternative embodiments, may use different circuit components or circuit implementations.

Figure 17:
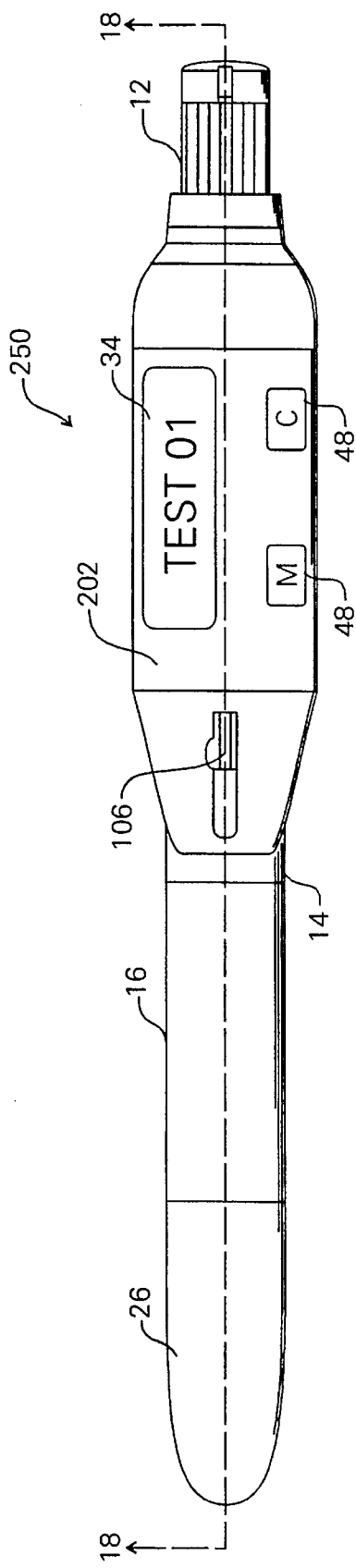
FIG. 17 shows a top view of another pen-type injector with a blood characteristic monitor in accordance with an embodiment of the present invention.
Figure 18:
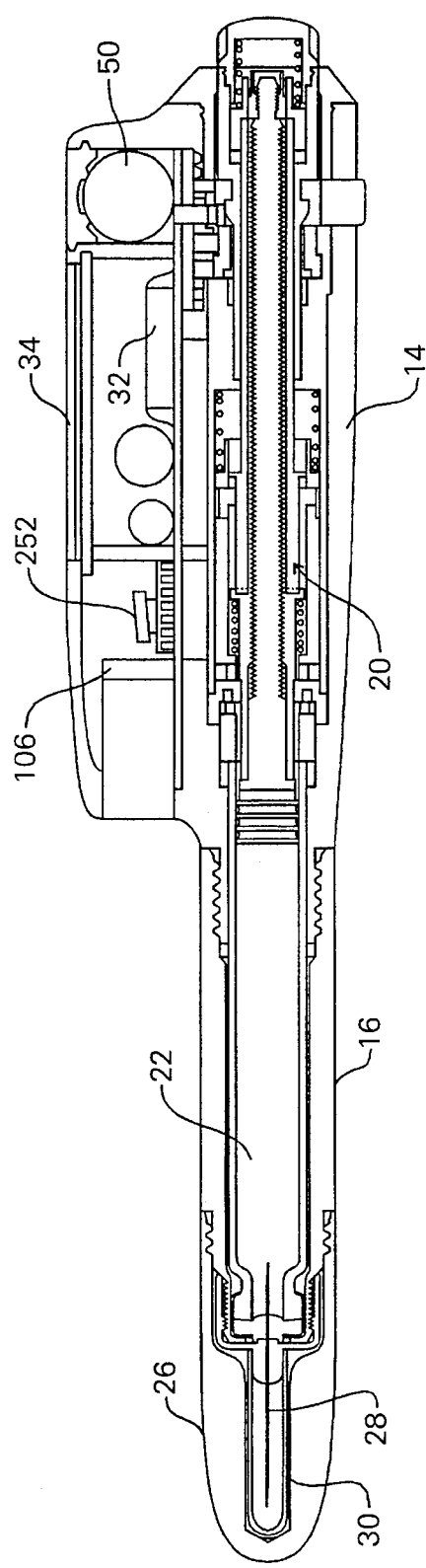
FIG. 18 is a cross-sectional view of the pen-type injector with a blood characteristic monitor as shown along the line 18—18 in FIG. 17.

FIGS. 17 and 18 show an alternative embodiment of a pen-type injector 250 coupled with a blood characteristic monitor 202. The pen-type injector 200 operates in a manner similar to the embodiments described-above with respect to FIGS. 14–16B. However, the test strip interface 206 is 90° offset with respect to the embodiment of FIGS. 14–16B, and the display 34 and the mode and clock setting panel 48 are arranged differently. FIG. 18 is a cross-sectional view of the pen-type injector 250 along the line 18—18 shown in FIG. 17. This view illustrates that the pen-type injector 250 can use the drive mechanism 20 described above with respect to the embodiments of FIGS. 1–13. Moreover, FIG. 18 illustrates the relative position of various internal components. For instance, the microprocessor 32, the battery 50, and a reaction chamber 252.

Figure 19:
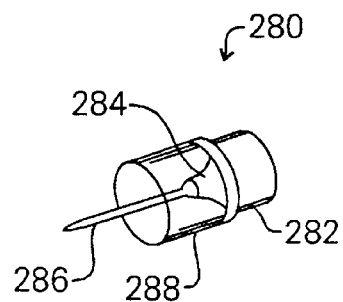
FIG. 19 is a perspective view of a disposable needle in accordance with an embodiment of the present invention.
Figure 20:
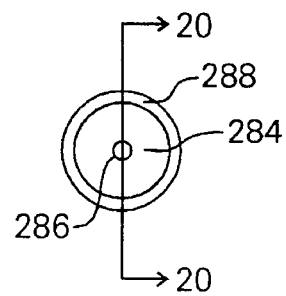
FIG. 20 is an end view of the disposable needle as shown in FIG. 19.
Figure 21:
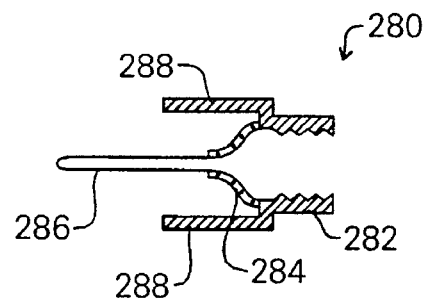
FIG. 21 is a cross-sectional view of the disposable needle as shown along the line 21—21 in FIG. 20.

FIGS. 19–21 show a preferred embodiment of a disposable needle 280 that substantially eliminates or reduces bleeding upon injection. The disposable needle 280 includes a threaded base 282, a needle support 284, a needle portion 286, and a hollow cylindrical cover 288. The threaded needle base 282 is adapted to be coupled to a pen-type injector as described above. However, in alternative embodiments, the needle base 282 may be attached by means of friction or the like, or the disposable needle 280 may be used with injectors other than pen-type injectors. A needle support 284 is coupled to the needle base 282 to hold the needle portion 286. Also coupled to the needle support 284 and the needle base 282 is the hollow cylindrical cover 288. The needle portion 286 is disposed inside the hollow cylindrical cover 288 such that the end of the needle portion 286 coupled to the needle support 284 cannot contact the skin during an injection. This prevents the needle support 284 from spreading the skin at the injection site. Spreading of the skin often results in bleeding. The needle portion 286 extends a sufficient distance beyond the hollow cylindrical cover 288 to allow for the proper administration of an injection. The hollow cylindrical cover helps the user insert the disposable needle 280 to the proper depth beneath the skin for an accurate injection. Moreover, the hollow cylindrical cover 288 tends to press the skin at the injection site together and this substantially eliminates or reduces bleeding at the injection site. The hollow cylindrical cover 288 also makes it easier for the user to attach and remove the disposable needle 280, and decrease the probability of being pricked during attachment and removal of the disposable needle 280.

Figure 22:
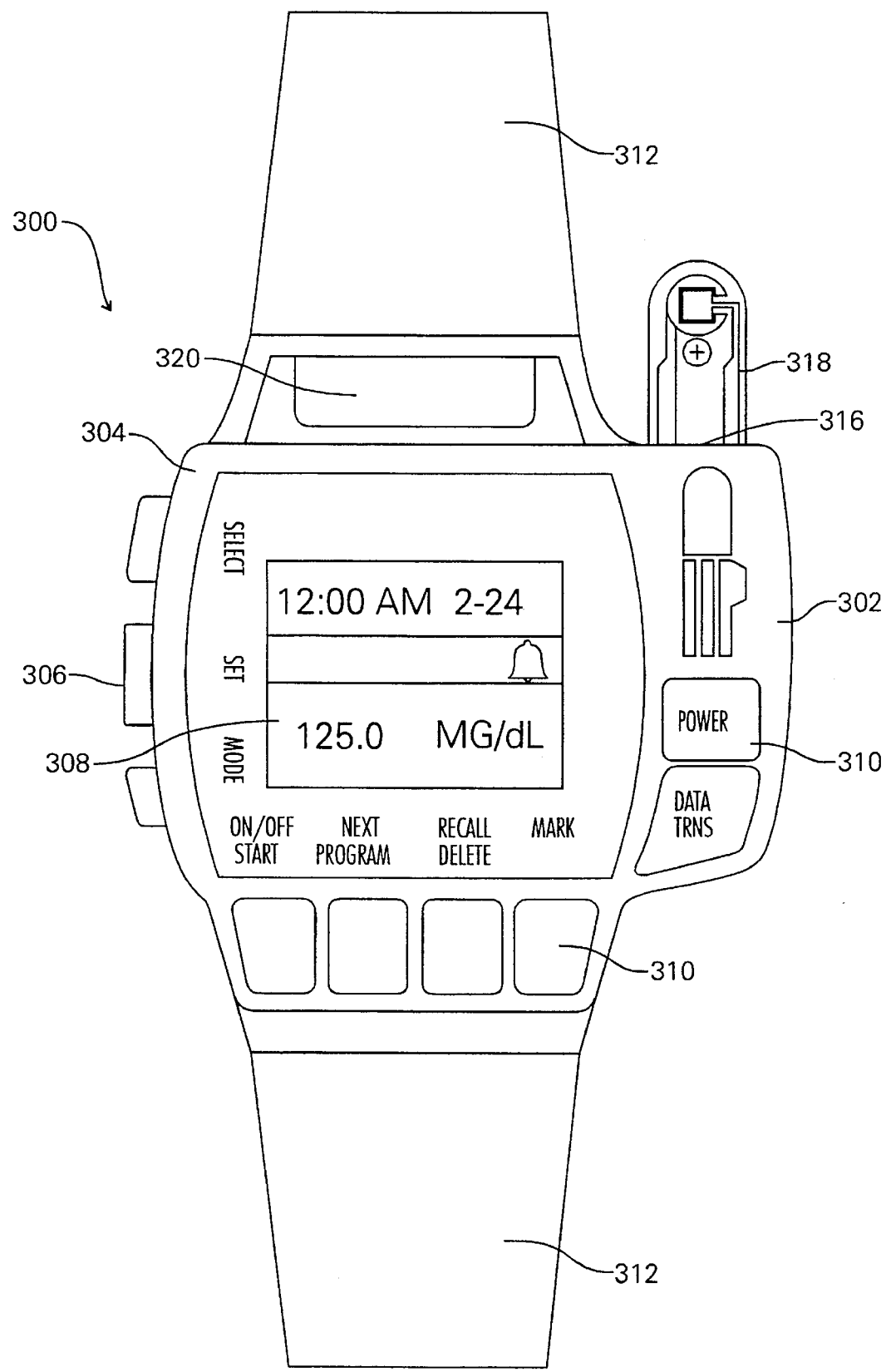
FIG. 22 is a front plan view of a blood characteristic monitor in accordance with an embodiment of the present invention.

FIG. 22 shows a blood characteristic monitor watch 300 in accordance with an embodiment of the present invention. The monitor watch 300 includes a blood characteristic monitor 302 and a wrist watch 304. The blood characteristic monitor 302 is contained with the housing of the wrist watch 304 to provide a portable self-contained blood testing device that is convenient to use and can record detailed blood sample results, as well as injection administration information. This provides detailed reporting that a doctor can use to determine compliance with a prescribed medical regimen.

The wrist watch 304 resembles a conventional LCD watch, in size and shape, and includes a watch setting key pad 306, a display 308, and a function and power/data key pad 310 for controlling the blood characteristic monitor 902. Inside the wrist watch 304 is a microprocessor 314 (see FIG. 23) that couples the key pads 306 and 310 to the blood-characteristic monitor 302 and the display 308. The wrist watch 304 is secured to the user's wrist by a pair of watch straps 312.

The blood characteristic monitor 302 includes a test strip interface 316 for receiving and analyzing a test strip 318. The blood characteristic monitor is activated by either insertion of a test strip 318 or the power/data key pad 310. The blood characteristic monitor 302 operates in a manner similar to that described above with respect to the embodiments of FIGS. 14–18. The results of the blood analysis are stored by the microprocessor 314 and may be recalled for later review on the display 308. In particular embodiments, the watch monitor 300 also includes a data input and output (I/O) port 320 which is activated and controlled by the microprocessor 314 and the power/data key pad 310 to upload program instructions and download information stored in a RAM 324 of the watch monitor 300. In preferred embodiments, the data I/O port 320 uses infrared (IR) technology; however, other data port technologies, such as cables or the like, may be used.

Figure 23:
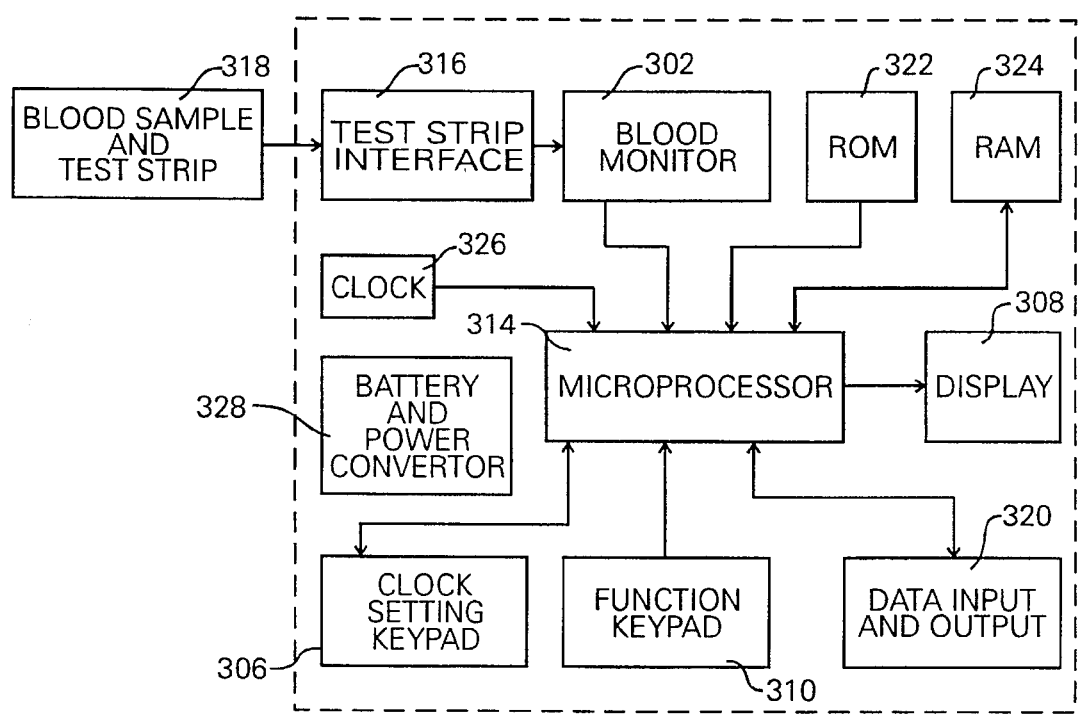
FIG. 23 is a simplified flow block diagram in accordance with the embodiment shown in FIG. 22.

FIG. 23 is a simplified block diagram of the watch monitor 300 with a blood characteristic monitor 302. A test strip 318 is fully inserted into the test strip interface 316 to activate the blood characteristic monitor 302. The blood characteristic monitor 302 analyzes the blood characteristics of the sample and sends the analysis results to the microprocessor 314, which displays the results on the display 308.

The microprocessor 314 is coupled to a ROM 322 and a RAM 324. In preferred embodiments, the ROM 322 is an EPROM and the RAM 324 is a static RAM; however, other comparable memory storage components may be used. The ROM 322 stores the programs used by the microprocessor 314 to determine various parameters, such as the correlation of results and the deviation from preset limits in a medical regimen, the date and the time, and how to report information to the user. The RAM 324 is used by the microprocessor 314 to store information about the blood analysis, as well as injections, for later recall by the user or the doctor. The microprocessor 314 also retrieves information from the RAM 324 so that a user or doctor can transcribe the stored information at a later time to determine compliance with the medical regimen and to spot trends requiring corrective action.

In preferred embodiments, the RAM 324 has a memory capacity for over 100 blood characteristic tests, 100 injection administration events, and memory to keep track of medication scheduling and special events. The microprocessor 314 is programmed to determine trends by comparing dosages administered by injections with the blood analysis results. These trends can be used by the microprocessor 314 to automatically recommend minor changes in the dosages within pre-programmed boundaries set by the doctor, or the trend results can be used by the doctor to directly adjust the dosages boundaries and the programs utilized by the microprocessor 314. This provides the doctor with greater control and flexibility over the user's medical regimen.

In preferred embodiments, the microprocessor 314 is coupled to a data input and output (I/O) port 320, and the user can download the stored information to an external computer (not shown) through the data I/O port 320. The data I/O port 320 is capable of transferring data in both directions so that updated program instructions or reminder alarms can be set by the user or doctor.

A clock setting key pad 306 is also coupled to the microprocessor 314 to provide the user with the capability to store additional information, set the date and the time, or set alarms on an internal clock 326 to indicate when to perform another blood analysis or administer an injection. In alternative embodiments, the microprocessor 314 may perform the internal clock functions without the necessity of a separate internal clock 326. The function key pad 310 also provide the capability to produce detailed reports and to interface with an external computer (not shown). The key pads 306 and 310 are used in conjunction with the display 308 to access the various modes and alarms utilizing methods typically employed to set the time on an LCD watch or the like. In preferred embodiments, the internal clock 326 of the watch monitor 300 is capable of multiple daily alarms, 12/24 hour formatting, and scrolling through a time zone map for easier record keeping during time zone changes.

The watch monitor 300 also includes a self contained battery and power convertor 328. The battery is a small watch type battery, or in preferred embodiments, the battery is a lithium battery capable of providing power for up to 5 years.

In preferred embodiments, the blood characteristic monitor 302 analyses a blood sample to determine the level of glucose in the blood and the blood characteristic monitor 302 uses an electro-chemical sensor technology such as described above with respect to the embodiments of FIGS. 14–18. A disposable (one time use) test strip 318 uses capillary action at the end of the test strip 318 to draw in a small amount of blood (typically 3 microliters) into a reaction chamber (not shown) of the test strip interface 316. When sufficient blood has been drawn into the reaction chamber, the testing sequence begins and a blood glucose reading is displayed on the display 308 in approximately 60 seconds from the start of the testing sequence. The blood characteristic monitor 302 provides blood glucose results from 40–500 mg/dl (2.2–27.8 mmol/L); however, other ranges may be used.

The blood characteristic monitor 302 is operated in substantially the same manner as described above with respect to the embodiments of FIGS. 14–18. The operator fully inserts the test strip 318 into the test strip interface 316 to turn on the blood characteristic monitor 302 and access the microprocessor 314. The blood characteristic analysis mode is activated and the microprocessor 314 causes the display 308 to display the previous test result and the time of the last test event. The user then places a blood sample (usually from a finger) on the end of the inserted test strip 318 which draws the sample into the reaction chamber of the test strip interface 316. In preferred embodiments, the blood monitor 302 beeps, or provides some other audible indication, when a sufficient sample has been drawn into the reaction chamber. After the beep, the test is conducted and is typically completed in about 60 seconds. Once the test is completed, the results are displayed on the display 308 and simultaneously stored by the microprocessor 314 in the RAM 324 for later recall. Removal of the test strip 318 automatically turns off the blood monitor 302 and returns the microprocessor 314 and the watch monitor 300 to the watch mode. If the user fails to remove the test strip 318, the microprocessor 314 sounds an alarm, and the blood monitor 302 is automatically turned off after 1 minute (although other time periods may be used). In alternative embodiments, other blood characteristic monitors may be used, such as a colormetric blood glucose meter, a dry membrane chemical reaction monitor or the like. Preferred embodiments utilize the above-described electro-chemical sensor technology in sensors produced by Matsushita Electronics of Japan and distributed by Miles Laboratories, Inc. However, alternative embodiments, may utilize a dry chemical sensor with an electro-chemical membrane by either Boehringer Manheim Corp of Indianapolis, Ind. or MediSense of Cambridge Mass.

FIGS. 24(a)–24(d) illustrate typical reports that can be obtained via the data I/O port 320 from the watch monitor 300. FIG. 24(a) shows a summary report of the blood analysis performed by the blood characteristic monitor 302. The readings are broken down into at least four basic time frames: breakfast, lunch, diner and snack. In preferred embodiments, the time frames may be further broken down into pre and post time frames. The report lists the number of blood analysis readings in each time frame, the standard deviation and the average value for the analyzed blood samples. FIG. 24(b) shows a detailed report of all the individual blood analysis events. The report provides the date, the day, the time and the results for each analyzed blood sample. Thus, this portion of the report allows the doctor or user to spot anomalous readings. FIG. 24(c) shows a detailed report on injections that have been administered and recorded by the user. The report provides the date, the day and the time of the injection. The report also recites how much of each type of insulin (regular (R) or intermediate (L)) was injected. This provides the doctor or user with information to compare blood analysis results with the amount of medication administered in the injection. FIG. 24(d) shows a detailed report on markers that are set and recorded by the user to indicate certain events or changes from the regular medical regimen. This provides the doctor or user with information that can aid in understanding and correlating otherwise anomalous results.

In preferred embodiments, test results can be deleted by pressing the delete button on the function key pad 310. This removes the results from the blood test average, for calibration or control test results, to prevent skewing the actual analysis information. The marker key on the function keypad 310 gives the user the option to store important information along with results already stored in the RAM 324. This can aid the user in recalling specific events or types of events that establish a trend. The marks are inserted by pressing the mark key and turning the blood characteristic monitor 302 off. Markers can be used to identify meal times, exercise times, injection events, or special circumstances and changes from the normal regimen.

In alternative embodiments, the watch monitor 300 can be used with a pen-type injector 10 described in the embodiment discussed above with respect to FIGS. 1–13. The data I/O port 320 of the watch monitor 300 can be utilized to download the injection information stored in the RAM 44 of the pen-injector 10. This simplifies the input of relevant injection data into the watch monitor 300.

FIGS. 25(a)–25(e) show a pen-type injector 400 with a blood characteristic monitor in accordance with an embodiment of the present invention. The pen-type injector 400 operates in a manner similar to the embodiments described-above with respect to FIGS. 14–18 and has the capabilities to provide the reports described in FIGS. 24(a)–24(d).

The pen-type injector 400 includes a detachable, protective cover and cap 402 that contains a storage area 404 for holding test strips 406 and a finger lancer mechanism 408 for obtaining a blood sample from the users finger. The cap 402 is snap fitted to the pen-type injector 400. However, in alternative embodiments, the cap 402 may be coupled to the pen-type injector 400 by different methods, such as hinges, adhesives, friction, detentes or the like.

A closed end 410 of the cap 402 supports a pen clip 412 and is snap fitted to the cap 402 to close off the end of the cap 402. When the closed end 410 is removed, the user has easy access to the storage area 404 and the finger lancer mechanism 408. In alternative embodiments, the closed end 410 of the cap 402 may be coupled to the cap 402 by different methods, such as hinges, adhesives, friction, detentes or the like.

Figure 25A:
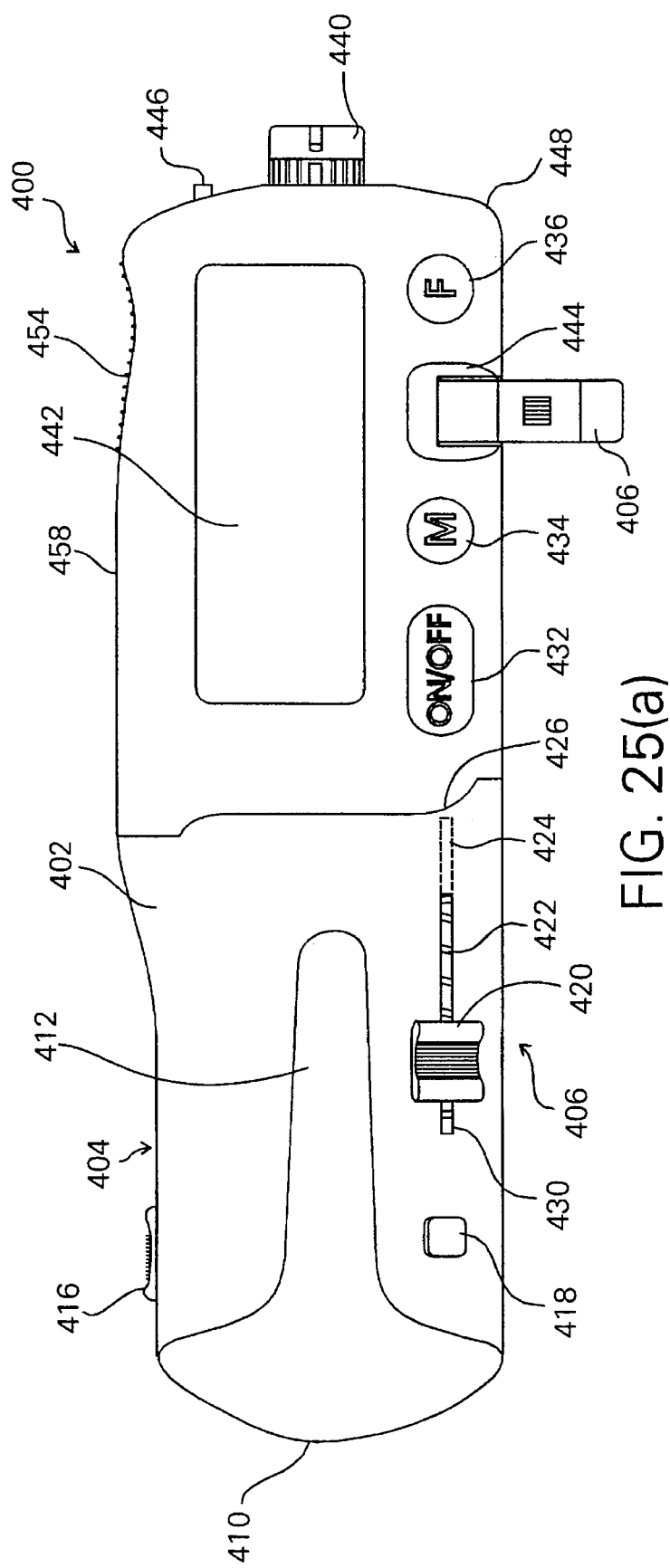

As shown in FIGS. 25(a), (b) and (e), the storage area 404 includes a leaf spring mechanism 414 and a slidable test strip supply button 416. Test strips 406 are loaded into the storage area 404 of the cap 402 through the opening produced when the closed end 410 of the cap 402 is removed. The user presses the leaf spring mechanism 414 down towards the center of the cap 402 away from the supply button 416, and the test strips 406 are then inserted between the leaf spring mechanism 414 and the supply button 416. The leaf spring 414 places the test strips 406 under sufficient pressure such that a single test strip 406 is ejected from the end of the cap 402 next to the pen-type injector 400 whenever the supply button 416 is slid towards the open end of the cap 402. Once a test strip 406 is ejected, the supply button 416 is slid back towards the closed end 410 of the cap 402 and the next test strip 406 is pressed into position to be ejected with the next sliding of the supply button 416. In alternative embodiments, different test strip 406 delivery systems may be used, such as a built in storage vial from which the user grasps and removes a single test strip 406, an electronic motorized test strip dispenser, a container for holding manufacturer's test strip shipment containers or the like.

Figure 25E:
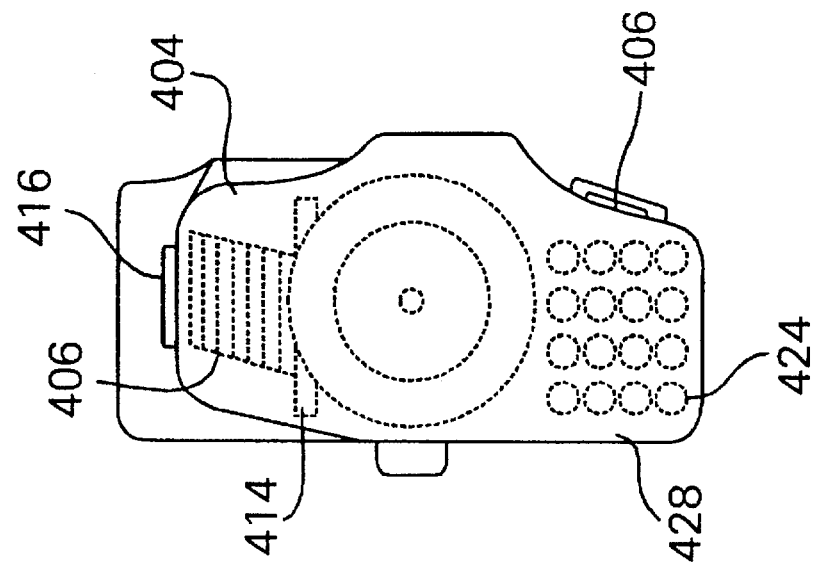
Figure 25D:
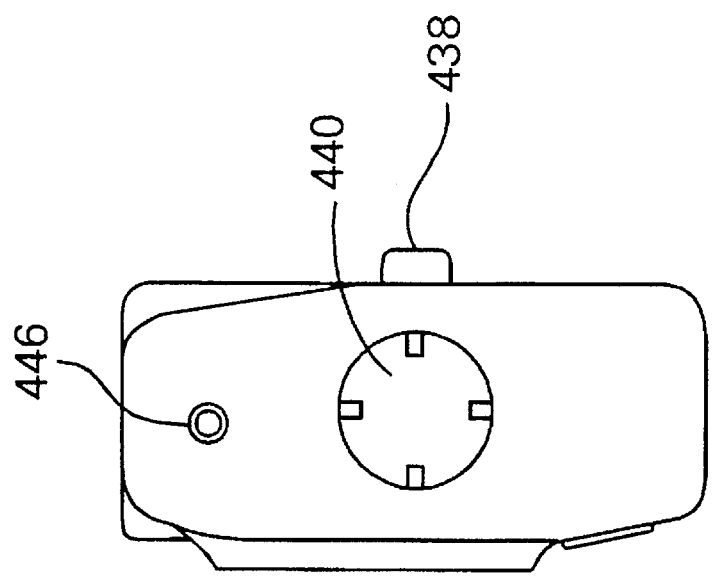

As shown in FIG. 25(a), the finger lancer mechanism 408 includes a release button 418, a tensioning and loading button 420, a spring 422 and a finger lancer 424 (shown in dashed lines in FIGS. 25(a)) and a form fitted lancer puncture site 426. Extra finger lancers 424 can be stored in a small storage compartment 428 in the cap 402 (as shown in FIG. 25(e)). Access to the storage compartment 428 is through the end of the cap 402 when the closed end 410 of the cap 402 is removed.

In preferred embodiments, a lancer is mounted to a lancer collet (not shown) at the end of the spring 424. When the loading button 420 is slid all the way towards the form fitted puncture site 426 it is locked in position and the lancer collet is loosened to allow removal of a used finger lancer 424 and the insertion of a new finger lancer 424. Once a new finger lancer 424 has been inserted into the lancer collet, the release button 418 is depressed and the loading button slides back to a neutral position as the tension on spring 422 is released.

To lance the finger and obtain a blood sample, the loading button 420 is slid towards the release button 418 until it is locked in position and a second lancing spring 430 is placed under sufficient pressure to drive the finger lancer 424 to puncture the finger of a user. Next, a user's finger is placed along side the form fitted puncture site 426. The user then depresses the release button 418. As the release button 418 is depressed the lancing spring 430 drives the finger lancer 424 forward to puncture the user's finger. After the finger lancer 424 is driven towards the puncture site 426, the spring 422 is placed under compressive tension to stop the forward movement of the finger lancer 424 after it has punctured the finger of the user. Then the spring 422 pushes the finger lancer 424 back inside the cap and away from the puncture site 426 until the loading button 420 is in a neutral position between the spring 422 and the lancer spring 430. After the user's finger is lanced, the user will place a drop of blood on a test strip 406 mounted in the blood monitor of the pen-type injector 400.

The pen-type injector 400 also includes an on/off button 432, a mode button 434, a function button 436, a start button 438, an actuator dosage knob 440, a display 442, a test strip interface 444 and a data port 446 that are all mounted in an injector housing 448. In preferred embodiments, the on/off button 432, mode button 434, function button 436, start button 438 and actuator dosage knob 440 operate in a manner similar to that described in the previous embodiments illustrated in FIGS. 1–24(d). Also, the display 442, the test strip interface 444 and data port 446 may use the same technology as described in the previous embodiments illustrated in FIGS. 1–24(d).

The pen-type injector 400 further includes a test strip code key interface 450 for receiving a code key 452 (see the cut-away section in FIG. 25(b)) that calibrates the blood monitor of the pen-type injector 400 for use with the batch of test strips 406 currently being stored in the storage area 404. In alternative embodiments, the blood monitor may be calibrated by accessing calibration codes that are stored in the memory of the pen-type injector 400.

The user depresses the on/off button 432 to activate the pen-type injector for either a blood test, to review data stored in the memory of the pen-type injector 400 or to transfer data between the pen-type injector 400 and an external computer (not shown). To deactivate the pen-type injector 400, the user depresses the on/off button 432 again. In preferred embodiments, if no functions or tests are performed within 1 minute (although longer or shorter times may be used), the pen-type injector 400 enters a "sleep mode" to conserve power. In the "sleep mode" the pen-type injector 400 can be reactivated by depressing a function 436 or mode 434 button, depression of the start button 438 or insertion of a test strip 406.

To perform a blood test, a user inserts a code key 452 into the code key interface 450 to calibrate the blood monitor of the pen-type injector 400 (see the cut-away of FIG. 25(*b*)). The code key 452 typically remains in the code key interface 450 until the current batch of test strips 406 in the storage area 404 are used up and a new batch is then inserted in the storage area 404. In alternative embodiments, the pen-type injector 400 may use a different calibration method, instead of a code key, such as a bar code reader, a data uplink or the like to provide calibration information for the blood monitor of the pen-type injector 400.

Once the blood monitor is calibrated, the user inserts a test strip 406 into the test strip interface 444. The blood monitor beeps or provides a visual indication on the display 442 that the test strip 406 has been properly inserted and that the blood monitor is now ready to perform a blood test. The user then applies a drop of blood to the end of the test strip 406. Capillary action or target membrane area saturation draws the blood up into the test strip interface 444. When sufficient blood has been drawn into the interface 444, the blood monitor again provides a beep or visual indication on the display 442 and commences the test. After the test is completed, the blood monitor provides a beep and visually displays the results on the display 442. If the results are acceptable, they are stored in memory, along with the date and time for later recall. If the test results were erroneous, an error message will be displayed on the display 444 and these will be stored in memory, unless the user deletes the results and error message within 1 minute (although longer or shorter times may be used) of the test being completed.

The user can use the mode button 434 and the function button 436 to program the pen-type injector 400. For example, the buttons can be used to set alarms or reminders, used to annotate stored test and injection data, used to set the time and date, or used to download data and upload instructions through the data port 446. The data port 446 utilizes a wired connection, such as an RS-232 standard to transfer data and instructions back and forth between the pen-type injector 400 and a computer (not shown). However, alternative embodiments can use other data transfer technology, such as infrared, radio waves or the like. In further alternatives, a bar code reader may be used.

To give an injection, the user depresses the start button 438 to release the dosage actuator knob 440. The user then rotates the actuator knob 440 to select a small dosage and performs an "air shot" to remove any air from the needle 28 and cartridge 22. If the user desires, the dosage amount and injection information for the air shot may be deleted before it is stored in memory or the injection may be marked as an "air shot." After the "air shot," the desired dosage is selected and the user performs an injection in a manner similar to that described in the embodiments illustrated in FIGS. 1–18. After the injection, the user can use the mode button 434 and function button 436 to annotate the injection information. The injection dosage, annotated information, date and time are stored and can be used to display or download the stored data to produce reports similar to those illustrated in FIGS. 24(*a*)–24(*d*).

The housing 448 of the pen-type injector 400 is ergonomically formed and shaped to fit easily in the user's hand for both blood characteristic testing and injections. The housing 448 also includes a gripping section 454 to facilitate control of the pen-type injector 400. In preferred embodiments, the housing 448 is formed from a plastic material and the gripping section 454 is formed by raised plastic ridges. In alternative embodiments, the housing 448 may be made out of different materials, such as metal, glass composites or the like, and the gripping section may use different textures or materials that are applied to the gripping section 454 of the pen-type injector 400.

As shown in FIG. 25(*b*), the housing 448 of the pen-type injector also includes a battery compartment for holding two disk shaped batteries, such as are commonly used in calculators, watches and blood monitoring equipment. However, alternative embodiments may utilize different types of batteries or external power sources. Location 458 represents a location where, for example, a jack for an external power source such as an AC adapter may be placed. In alternative embodiments, a different type of data port 446 may be placed in location 458. For example, a bar code reader or IR port could be placed in this location 458 for easy uploading and downloading of data.

Figure 26A:
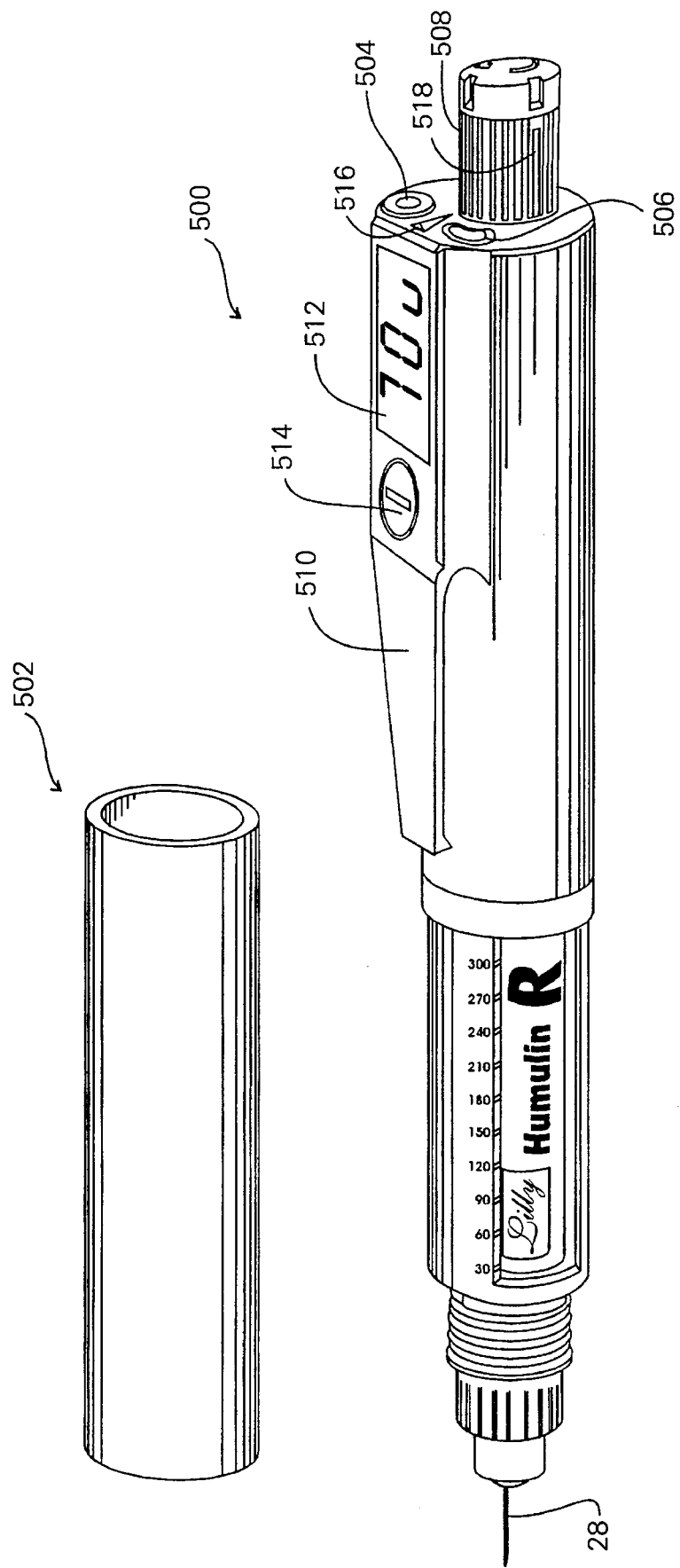
FIGS. 26(a)–26(c) are views of a pen-type injector in accordance with an embodiment of the present invention.
Figure 26B:
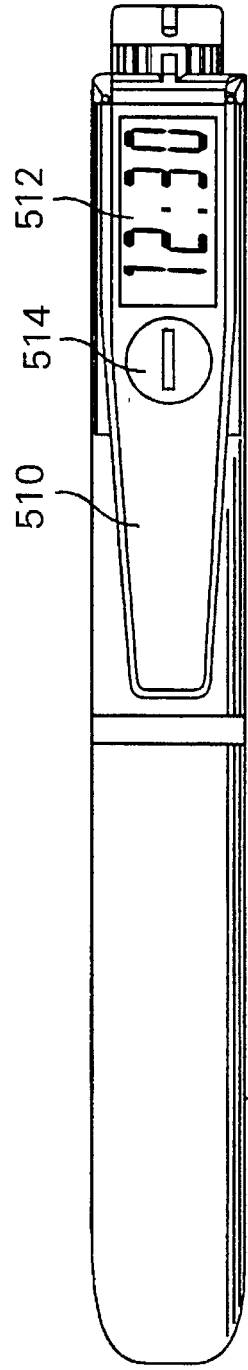
Figure 26C:
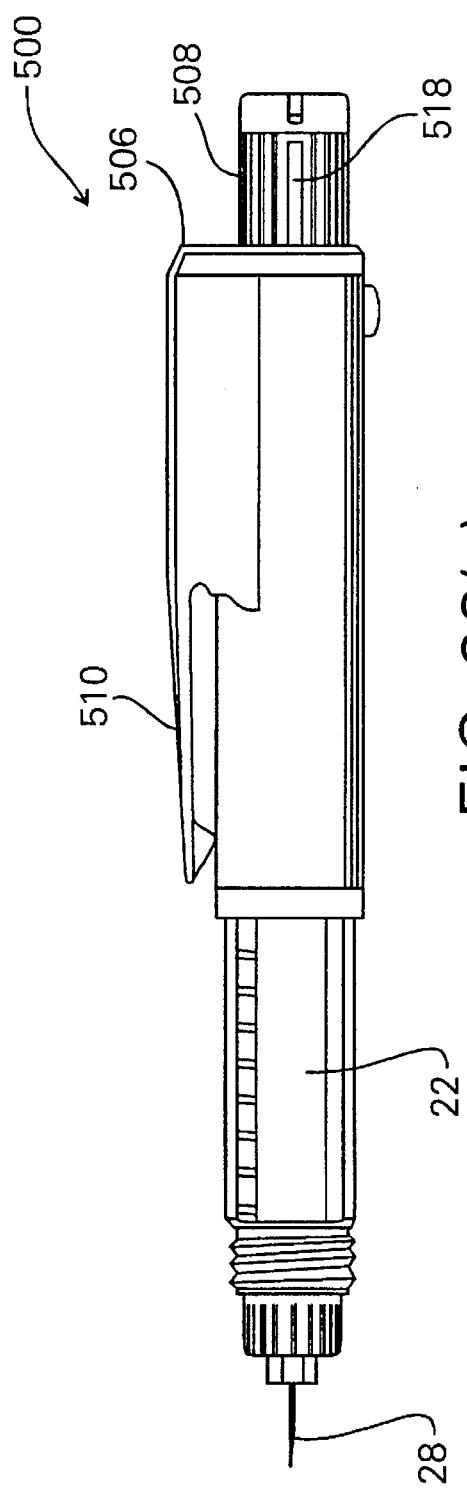

FIGS. 26(*a*)–26(*c*) show a pen-type injector 500 in accordance with an embodiment of the present invention. The pen-type injector 500 operates in a manner similar to the embodiments described-above with respect to FIGS. 1–13 and has the capabilities to provide the report described in FIG. 24(*c*).

The pen-type injector 500 includes a cap 502 for easy removal and covering of the needle 28 and the pen-type injector 500. In the illustrated embodiment, the mode button 504 and the function button 506 have been placed at the end of the pen-type injector 500 near a dosage knob 508. This provides additional space on a pen clip 510 for a larger display 512 that is easier to read by elderly users or patients that have difficulty reading small numbers. The pen clip 510 also contains a battery compartment 514 for holding the batteries required to operate the pen-type injector 500. Locating the battery compartment 514 on the pen clip 514 facilitates changing of the batteries, since it is readily accessible and the user can use a screwdriver, nail file, dime or the like to unscrew the cover of the battery compartment 514. The pen-type injector 500 also includes a position indicator 516 that aids the user in setting the dosage. The indicator 516 represents one dosage increment (or decrement) each time the indentations 518 are rotated past the indicator 516. In alternative embodiments, audio indicators or other visual indicators may be used.

Various aspects of the illustrated embodiments may be combined in different ways. For example, the reports generated by the watch monitor 300 may be produced by the pen-type injector 10, the combination pen-type injector 200, the combination pen-type injector 400, and the pen-type injector 500. The various features such as alarms, test strip storage and lancers may also be combined with the various embodiments.

Also various other types of medication delivery devices, such as medication pumps, jet injectors, inhalers, sprays or the like may be used. For example, particular embodiments may use a medication pump injection mechanism that is worn by the patient during the day, and which has a receptacle for storing fluid that is injected manually or by a pre-set timed sequence. The medication is delivered through a tube that is attached to the pump delivery mechanism at one end and a shunt that is temporarily connected to the patient's body at the other end of the tube. The medication pump is combined with a processor so that insulin or the like is delivered by the pump and the processor stores relevant information about the medication delivered. Also, the processor is coupled to a characteristic monitor, which is used to determine the characteristics of a sample from the patient and to store the information with the processor coupled to the medication pump. In particular embodiments, the medication pump can use removable pre-measured, pre-filled disposable or rechargeable ampules of medication.

In another alternative embodiment, a portable, hand-held pneumatic or compression spring-assisted medical injection delivery mechanism such as a "jet" injector or the like is used to inject a medication. Particular embodiments use a needle or high pressure needle-less stream that pierces the skin at the injection site to deliver the injection subcutaneously or intermuscularly. In further embodiments, the injection device may use a needle which allows the user to extract a measurable amount of medication from a storage canister or ampule, and receive it in a delivery chamber of the device that is similar to a syringe chamber. Alternatively, the injection device can use removable pre-measured, pre-filled disposable or rechargeable ampules of medication. In preferred embodiments, the injection device can also be coupled to a processor for storing information about the injection and a characteristic monitor for analyzing and storing characteristics from a sample taken from the patient's body.

In another alternative embodiment, a portable, hand-held medical nasal inhaler spray which has a receptacle capable of holding a pre-filled cartridge, vial, or pressurized container of mediation is used to deliver a dosage of medication. Particular embodiments, may use a manual or an automatically regulated and controlled delivery mechanism for administering the medication via drip or atomized nasal spray. The inhaler or spray can use removable pre-measured, pre-filled disposable or rechargeable ampules of medication. The inhaler or spray is coupled to a processor to determine and store the amount of medication that is delivered. In preferred embodiments, the inhaler or spray is also coupled to a characteristic monitor for analyzing and storing characteristics from a sample taken from the patient's body.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A portable, hand-held medical device for use by a patient, the medical device comprising:
   an external hand-held medication delivery mechanism for manually administering a dosage of a medication, the medication delivery mechanism only contacting the patient's body when a dosage of medication is administered;
   a hand-held blood characteristic monitor for analyzing a blood sample removed from the patient's body and the sample being placed into contact with the characteristic monitor for analysis external to the body of the patient;
   a processor coupled to the hand-held medication delivery device and the hand-held characteristic monitor, wherein the processor determines a value equal to the dosage of the medication to be administered by the hand-held medication delivery device, and wherein the processor determines characteristics from the blood sample analyzed by the hand-held characteristic monitor; and
   a single hand-held housing shaped and sized to fit in a shirt pocket, the housing holding the medication delivery mechanism, characteristic monitor and the processor.

2. A device according to claim 1, further including a data port coupled to the processor that is used to transfer program instructions from an external programming device to the processor.

3. A device according to claim 1, wherein the blood sample is taken from the patient's body at a location that is different from a location where the medication is administered.

4. A device according to claim 1, further including a memory device coupled to the processor to store the value equal to the dosage and the characteristics determined by the processor.

5. A device according to claim 4, further including a receptacle capable of holding the medication and a delivery mechanism having an actuator knob for setting the dosage of the medication to be administered by the hand-held medication delivery device and a drive mechanism coupled between the actuator knob and the receptacle to administer the set dosage of the medication, wherein the actuator knob of the delivery mechanism triggers the drive mechanism to administer the medication held in the receptacle.

6. A device according to claim 4, further including a data port coupled to the processor that is used to transfer the value equal to the dosage stored in the memory device to an external data collection device.

7. A device according to claim 4, further including a display device coupled to the processor to display the value equal to the dosage and the characteristics determined by the processor.

8. A device according to claim 7, further including a clock circuit coupled to the processor for determining a time, wherein the time is stored in the memory device with the value equal to the dosage and the characteristics determined by the processor, and wherein the time is displayed on the display device.

9. A device according to claim 1, wherein the blood sample is taken from the patient's finger.

10. A portable medical device, comprising:
    an external hand-held medication injector for manually injecting a dosage of a medication, the medication injector only contacting a patient's body when a dosage of medication is injected;
    a hand-held blood characteristic monitor for analyzing a blood sample removed from the patient's body and the sample being placed into contact with the characteristic monitor for analysis external to the body of the patient, wherein the hand-held blood characteristic monitor is coupled to the hand-held medication injector;
    a processor coupled to the hand-held medication injector and the hand-held blood characteristic monitor to form a single device, wherein the processor determines a value equal to the dosage of the medication to be injected by the hand-held medication injector, and wherein the processor determines blood characteristics from the blood sample analyzed by the hand-held blood characteristic monitor; and
    a single pen-type housing holding the medication injector, the blood characteristic monitor and the processor.

11. A device according to claim 10, further including a data port coupled to the processor that is used to transfer program instructions from an external programming device to the processor.

12. A device according to claim 10, wherein the blood sample is taken from the patient's body at a location that different from a location where the medication is administered.

13. A device according to claim 10, wherein the blood sample is taken from the patient's finger.

14. A device according to claim 10, further including a data port coupled to the processor that is used to transfer program instructions from an external programming device to the processor.

15. A device according to claim 14, wherein the data port uses infrared energy to transfer the program instructions.

16. A device according to claim 10, further including a memory device coupled to the processor to store the value equal to the dosage and the blood characteristics determined by the processor.

17. A device according to claim 16, wherein the medication injector includes a receptacle capable of holding the medication and an injection mechanism having an actuator knob for setting the dosage of the medication to be administered by the hand-held medication injector and a drive mechanism coupled between the actuator knob and the receptacle to inject the set dosage of the medication, wherein the actuator knob of the injection mechanism triggers the drive mechanism to administer the injection of the medication held in the receptacle.

18. A device according to claim 16, further including a data port coupled to the processor that is used to transfer the value equal to the dosage stored in the memory device to an external data collection device.

19. A device according to claim 16, further including a display device coupled to the processor to display the value equal to the dosage and the blood characteristics determined by the processor.

20. A device according to claim 19, further including a clock circuit coupled to the processor for determining a time, wherein the time is stored in the memory device with the value equal to the dosage and the blood characteristics determined by the processor, and wherein the time is displayed on the display device.

21. A device according to claim 20, wherein the clock circuit further includes means to determine the date.

22. A device according to claim 20, wherein the clock circuit further includes means to provide an alarm indication at a predetermined time.

23. A device according to claim 10, further including a clock and a memory storage device coupled to the processor for storing a measure of time from the clock and the blood characteristics determined by the processor.

24. A device according to claim 23, further including a display device coupled to the processor to display the measure of the time from the clock and the blood characteristics determined by the processor.

25. A device according to claim 23, further including a data port coupled to the processor that is used to transfer the measure of the time and the blood characteristics stored in the memory device to an external data collection device.

26. A device according to claim 25, wherein the data port uses infrared energy to transfer the measure of the time and the blood characteristics stored in the memory storage device.

27. A portable medical device to maintain and monitor a condition of an individual's body, the device comprising:

an external hand-held injector for manually injecting a dosage of an injectable substance into the individual's body, the injector only contacting the individual's body when a dosage of injectable substance is injected;

a hand-held characteristic monitor for analyzing a characteristic of the individual's body, the characteristic monitor measuring and performing an analysis external to the individual's body, wherein the hand-held characteristic monitor is coupled to the hand-held injector;

a processor coupled to the hand-held injector and the hand-held characteristic monitor to form a single all-in-one device, wherein the processor determines a value equal to the dosage of the injectable substance to be injected by the hand-held injector into the individual's body, and wherein the processor determines sample characteristics from the sample analyzed by the hand-held characteristic monitor; and a single housing shaded and sized to fit in a shirt pocket, the housing holding the injector, the characteristic monitor and the processor, wherein the characteristic monitor held by the housing is located away from the injector such that the characteristic of the individual's body is obtained at a location different from a location where the injectable substance is injected into the individual's body.

28. A device according to claim 27, further including a data port coupled to the processor that is used to transfer program instructions from an external programming device to the processor.

29. A device according to claim 27, wherein the characteristic is obtained from the patient's body at a location that is different from a location where the medication is administered.

30. A device according to claim 27, wherein the characteristic is obtained from the patient's finger.

31. A device according to claim 27, wherein the single housing is adapted to be easily held and used in a hand or transported in a pocket.

32. A device according to claim 27, further including a data port coupled to the processor that is used to transfer program instructions from an external programming device to the processor.

33. A device according to claim 32, wherein the data port uses infrared energy to transfer the program instructions.

34. A device according to claim 27, further including a clock and a memory storage device coupled to the processor for storing a measure of time from the clock and the sample characteristics determined by the processor.

35. A device according to claim 34, further including a display device coupled to the processor to display the measure of the time from the clock and the sample characteristics determined by the processor.

36. A device according to claim 34, further including a data port coupled to the processor that is used to transfer the measure of the time and the sample characteristics stored in the memory device to an external data collection device.

37. A device according to claim 36, wherein the data port uses infrared energy to transfer the measure of the time and the sample characteristics stored in the memory device.

38. A device according to claim 27, further including a memory device coupled to the processor to store the value equal to the dosage and the sample characteristics determined by the processor.

39. A device according to claim 38, wherein the hand-held injector includes a receptacle capable of holding the injectable substance and an injection mechanism having an actuator knob for setting the dosage of the injectable substance to be administered by the hand-held injector and a drive mechanism coupled between the actuator knob and the receptacle to inject the set dosage of the injectable substance, wherein the actuator knob of the injection mechanism triggers the drive mechanism to administer the injection of the injectable substance held in the receptacle.

40. A device according to claim 38, further including a data port coupled to the processor that is used to transfer the value equal to the dosage stored in the memory device to an external data collection device.

41. A device according to claim 38, further including a display device coupled to the processor to display the value equal to the dosage and the sample characteristics determined by the processor.

42. A device according to claim 41, further including a clock circuit coupled to the processor for determining a time, wherein the time is stored in the memory device with the value equal to the dosage and the sample characteristics determined by the processor, and wherein the time is displayed on the display device.

43. A device according to claim 42, wherein the clock circuit further includes means to determine the date.

44. A device according to claim 42, wherein the clock circuit further includes means to provide an alarm indication at a predetermined time.

* * * * *